United States Patent
Dhar et al.

(10) Patent No.: US 10,004,809 B2
(45) Date of Patent: Jun. 26, 2018

(54) PRECISE DELIVERY OF THERAPEUTIC AGENTS TO CELL MITOCHONDRIA FOR ANTI-CANCER THERAPY

(71) Applicant: UNIVERSITY OF GEORGIA RESEARCH FOUNDATION, INC., Athens, GA (US)

(72) Inventors: Shanta Dhar, Athens, GA (US); Rakesh Pathak, Athens, GA (US)

(73) Assignee: University of Georgia Research Foundation Inc., Athens, GA (US)

( * ) Notice: Subject to any disclaimer, the term of this patent is extended or adjusted under 35 U.S.C. 154(b) by 56 days.

(21) Appl. No.: 14/902,514

(22) PCT Filed: Jul. 1, 2014

(86) PCT No.: PCT/US2014/045131
§ 371 (c)(1),
(2) Date: Dec. 31, 2015

(87) PCT Pub. No.: WO2015/002996
PCT Pub. Date: Jan. 8, 2015

(65) Prior Publication Data
US 2016/0339106 A1    Nov. 24, 2016

Related U.S. Application Data

(60) Provisional application No. 61/841,657, filed on Jul. 1, 2013.

(51) Int. Cl.
| | | |
|---|---|---|
| *C07F 9/54* | (2006.01) |
| *A61K 47/48* | (2006.01) |
| *A61K 47/59* | (2017.01) |
| *A61K 47/54* | (2017.01) |
| *A61K 45/06* | (2006.01) |
| *A61K 31/663* | (2006.01) |
| *A61K 31/675* | (2006.01) |
| *C07F 9/6518* | (2006.01) |
| *A61K 9/51* | (2006.01) |

(52) U.S. Cl.
CPC ...... *A61K 47/48023* (2013.01); *A61K 9/5146* (2013.01); *A61K 9/5184* (2013.01); *A61K 31/663* (2013.01); *A61K 31/675* (2013.01); *A61K 45/06* (2013.01); *A61K 47/482* (2013.01); *A61K 47/54* (2017.08); *A61K 47/593* (2017.08); *C07F 9/5442* (2013.01); *C07F 9/65181* (2013.01)

(58) Field of Classification Search
CPC .................................................. C07F 9/5442
See application file for complete search history.

(56) References Cited

U.S. PATENT DOCUMENTS

| | | | |
|---|---|---|---|
| 7,714,016 B2 | 5/2010 | Gangwar et al. |
| 2009/0118370 A1 | 5/2009 | Michelakis et al. |
| 2010/0260676 A1 | 10/2010 | Hanson |
| 2011/0059922 A1 | 3/2011 | Zarling et al. |
| 2012/0157385 A1 | 6/2012 | Selwood et al. |
| 2013/0017265 A1 | 1/2013 | Farokhzad et al. |

FOREIGN PATENT DOCUMENTS

| | | |
|---|---|---|
| WO | 2006010077 A2 | 1/2006 |
| WO | 20090036092 A2 | 3/2009 |
| WO | 2012051306 A2 | 4/2012 |
| WO | 2013033513 A1 | 3/2013 |

OTHER PUBLICATIONS

Babu, et al., "Role of SLC5A8, a plasma membrane transporter and a tumor suppressor, in the antitumor activity of dichloroacetate", Oncogene 2011, 30, 4026-4037.
Benedettini, E., et al., "The pathogenesis of prostate cancer: from molecular to metabolic alterations", Diagn. Histopathol. 2008, 14, 195-201.
Bonnet, S., et al., " A mitochondria-K+ channel axis is suppressed in cancer and its normalization promotes apoptosis and inhibits cancer growth", Cancer Cell 2007, 11, 37-51.
Cheong, H., et al., "Therapeutic targets in cancer cell metabolism and autophagy", Nat. Biotechnol. 2012, 30, 671-678.
Coady, M.J., et al., "The human tumor suppressor gene SLC5A8 expresses a Na+-monocarboxylate cotransporter", J. Physiol. 2004, 557, 719-731.
Dhar, S., et al., "Mitaplatin, a potent fusion of cisplatin and the orphan drug dichloroacetate", Proc. Natl. Acad. Sci. USA 2009, 106, 22199-22204.
Dhar, S., et al., "Selective detection and quantification of oxidized a basic lesions in DNA", J. Am. Chem. Soc. 2007, 129, 8702-8703.
Dietl, K., et al., "Lactic acid and acidification inhibit TNF secretion and glycolysis of human monocytes", J. Immunol. 2010, 184, 1200-1209.
Fischer, K., et al., "Inhibitory effect of tumor cell-derived lactic acid on human T cells", Blood 2009, 109, 3812-3819.
Gabrilovich, D.I., et al., "Production of vascular endothelial growth factor by human tumors inhibits the functional maturation of dendritic cells", Nat. Med. 1996, 2, 1096-1103.
Gatenby, R.A., et al., "Why do cancers have high aerobic glycolysis?", Nat. Rev. Cancer 2004, 4, 891-899.
Gottfried, E., et al., "Tumor-derived lactic acid modulates dendritic cell activation and antigen expression.", Blood 2006, 107, 2013-2021.
Helman, L.J., et al., "Mechanisms of sarcoma development", Nat. Rev. Cancer 2003, 3, 685-694.
Higgins, L.H., "Hypoxia and the metabolic phenotype of prostate cancer cells", Biochim. Biophys. Acta 2009, 1787, 1433-1443.

(Continued)

*Primary Examiner* — Joseph R Kosack
(74) *Attorney, Agent, or Firm* — Meunier Carlin & Curfman LLC

(57) ABSTRACT

Described is a targeted molecular scaffold for construction of a metabolic inhibitor loaded with cancer-cell specific activity and anti-tumor immunity. Incorporation of a mitochondria targeting moiety such as triphenylphosphonium cation through a biodegradable linker in allowed for mitochondria targeting of certain metabolic inhibitors like dichloroacetic acid (DCA).

8 Claims, 9 Drawing Sheets

(56) References Cited

OTHER PUBLICATIONS

Jackson, V.N, et al., "The kinetics, substrate, and inhibitor specificity of the monocarboxylate (lactate) transporter of rat liver cells determined using the fluorescent intracellular pH indicator, 2',7'-bis(carboxyethyl)-5(6)-carboxyfluorescein.", J. Biol. Chem. 1996, 271, 861-868.

Kato, M., et al., "Distinct structural mechanisms for inhibition of pyruvate dehydrogenase kinase isoforms by AZD7545, dichloroacetate, and radicicol", Structure 2007, 15, 992-1004.

Kim, J.W., et al., "Cancer's molecular sweet tooth and the Warburg effect", Cancer Res. 2006, 66, 8927-8930.

Kim, R., et al., "Cancer immunoediting from immune surveillance to immune escape", Immunology 2007, 121, 1-14.

Lamont, A.G., et al., "IL-12: a key cytokine in immune regulation", Immunol. Today 1996, 17, 214-217.

Li, H., et al., "SLC5A8, a sodium transporter, is a tumor suppressor gene silenced by methylation in human colon aberrant crypt foci and cancers", Proc. Natl. Acad. Sci. USA 2003, 100, 8412-8417.

Marrache, S., et al., "Biodegradable synthetic high-density lipoprotein nanoparticles for atherosclerosis", Proc. Natl. Acad. Sci. USA, 2013.

Marrache, S., et al., "Engineering of blended nanoparticle platform for delivery of mitochondria-acting therapeutics", Proc. Natl. Acad. Sci. USA 2012, 109, 16288-16293.

Marrache, S., et al., "Immune stimulating photoactive hybrid nanoparticles for metastatic breast cancer", Integr. Biol. 2013, 5, 215-223.

Miyauchi, S., et al., "Functional identification of SLC5A8, a tumor suppressor down-regulated in colon cancer, as a Na(+)-coupled transporter for short-chain fatty acid", J. Biol. Chem. 2004, 279, 13293-13296.

Orsini, E., et al., "The circulating dendritic cell compartment in patients with chronic lymphocytic leukemia is severely defective and unable to stimulate an effective T-cell response", Cancer Res. 2003, 63, 4497-4506.

Pathak, et al., "Mito-DCA: A Mitochondria Targeted Molecular Scaffold for Efficacous Delivery of Metabolic Modulator Dichloroacetate", ACS Chem. Biol. 2014, 9, (5), 1178-1187.

Pearson, H., et al., "Cancer patients opt for unapproved drug", Nature 2007, 446, 474-475.

Perry, S.W., et al., "Mitochondrial membrane potential probes and the proton gradient: a practical usage guide", BioTechniques 2001, 50, 98-115.

Rabinovich, G.A., et al., "Immunosuppressive strategies that are mediated by tumor cells", Annu. Rev. Immunol. 2007, 25, 267-296.

Radmayr, C., et al., "Dendritic antigen-presenting cells from the peripheral blood of renal-cell-carcinoma patients", Int. J. Cancer 1995, 63, 627-632.

Ross, M.F., et al., "Rapid and extensive uptake and activation of hydrophobic triphenylphosphonium cations within cells", Biochem. J. 2008, 411, 633-645.

Samudio, I., et al., "Mitochondrial uncoupling and the Warburg effect: molecular basis for the reprogramming of cancer cell metabolism", Cancer Res. 2009, 69, 2163-2166.

Smith, R.A., et al.,"Delivery of bioactive molecules to mitochondria in vivo", Proc. Natl. Acad. Sci. USA 2003, 100, 5407-5412.

Stockwin, L.H., et al.,"Sodium dichloroacetate selectively targets cells with defects in the mitochondrial", Int. J. Cancer 2010, 127, 2510-2519.

Sun, R.C., et al., "Reversal of the glycolytic phenotype by dichloroacetate inhibits metastatic breast cancer cell growth in vitro and in vivo", Breast Cancer Res. Treat. 2010, 120, 253-260.

Warburg, O., "On the origin of cancer cells", Science 1956, 123, 309-314.

Zu, X.L., et al., "Cancer metabolism: facts, fantasy, and fiction",Biochem. Biophys. Res. Commun. 2004, 313, 459-465.

International Search Report and Written Opinion for PCT/US2014/045131 dated Dec. 10, 2014.

Extended European Search Report for EP14819395.6 dated Jan. 9, 2017.

PRECISE DELIVERY OF THERAPEUTIC AGENTS TO CELL MITOCHONDRIA FOR ANTI-CANCER THERAPY

ACKNOWLEDGEMENT OF GOVERNMENT SUPPORT

This invention was made with government support under grant GM092378 awarded by the National Institutes of Health and grant W81XWH-12-1-0406 awarded by the Department of Defense. The government has certain rights in the invention.

BACKGROUND

Stimulation of mitochondrial activity and alterations of cancer cell characteristic adenosine-5'-triphosphate (ATP) generation pathways is an anticancer strategy. (Warburg, *Science* 123:309-314, 1956; Zu et al., *Biochem. Biophys. Res. Commun.* 313:459-465, 2004; Samudio et al., *Cancer Res.* 69:2163-2166, 2009; Gatenby et al., *Nat. Rev. Cancer* 4:891-899, 2004; Kim et al., *Cancer Res.* 66:8927-8930, 2006; Cheong et al., *Nat. Biotechnol.* 30:671-678, 2012.) The molecule dichloroacetate (DCA) has the potential to become a major player in the field of cancer chemotherapy. (Bonnet et al., *Cancer Cell* 11:37-51, 2007; Dhar et al., *Proc. Natl. Acad. Sci. USA* 106:22199-22204, 2009; Sun et al., *Breast Cancer Res. Treat.* 120:253-260, 2010; Pearson, *Nature* 446:474-475, 2007.) By utilizing the metabolic switch, DCA reverses the abnormal cancer cell metabolism from aerobic glycolysis to glucose oxidation by reducing the activity of mitochondrial pyruvate dehydrogenase kinase 1 (PDK1), which negatively regulates pyruvate dehydrogenase (PDH) causing pyruvate to convert to acetyl-CoA promoting oxidative phosphorylation (Bonnet et al. 2007). DCA reduces the high mitochondrial membrane potential ($\Delta\psi_m$) of cancer cells and increases mitochondrial reactive oxygen species (ROS) in malignant, but not in normal cells (Id.). However, therapeutically prohibitive high DCA doses are needed for suppression of tumor growth due to the lack of effective mechanisms for DCA entry into tumor cells and its localization inside the target organelle, mitochondria of cells.

One study demonstrated that extremely high concentrations of DCA are needed to induce selective tumor cell death at a concentration that has no toxic effect on normal cells (Stockwin et al., *Int. J. Cancer* 127:2510-2519, 2010). In physiological condition, orally or intravenously administered DCA is ionized and cannot pass through the plasma membrane by passive diffusion. Methods and compositions that allow introduction of physiologically relevant doses of DCA, as well as other therapeutics, into cancer cells are needed. Also needed are methods and compositions that allow the anionic form of DCA to cross the negatively charged inner mitochondrial membrane (IMM) to access PDK1 within the mitochondrial matrix. Such methods and compositions would be very useful in anti-cancer therapies. Moreover, such methods and compositions could be applied to other therapeutic agents besides DCA, which could also benefit from targeted delivery into the mitochondria. The compositions and methods disclosed here address these and other needs.

SUMMARY

In accordance with the purposes of the disclosed compounds, compositions, and methods, as embodied and broadly described herein, the disclosed subject matter relates to compositions and methods of making and using the compositions. In other aspects, disclosed herein are compounds having Formula I:

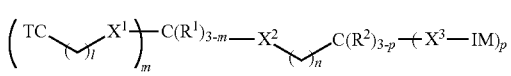

where "TC" is a mitochondria targeting moiety; "IM" is an inhibitor moiety; l is from 1 to 10; m is from 1 to 3; n is from 0 to 20; p is from 1 to 64; $X^1$ is $-CO_2-$, $-CO_2CH_2-$, $-CONR^3-$, $-SO_2NR^3-$, $-CHR^3-$, $-NHR^3-$, $-CO-$, or $-O-$; $X^2$ is $-CONR^3-$, $-SO_2NR^3-$, $-CHR^3-$, $-NHR^3-$, $-CO-$, or $-O-$; $X^3$ is a suitable linker depending on the available site on the particular inhibitor of interest, e.g., $-CO_2-$, $-OC(O)-$, $-NHR^3-$, $-SO_2-$, $-CO-$, $-S-$, $-O-$, -1,2,3-triazole-; and $R^1$, $R^2$, and $R^3$ are, independently of one another, $-H$, $-F$, $-Cl$, $-Br$, $-OH$, $-C_{1-6}$ alkyl, or $-OC(O)C_{1-6}$ alkyl, or a pharmaceutically acceptable salt thereof. Specific subgenera of Formula I, such as Formulas II-V, are disclosed herein. Compounds of Formula VI are also disclosed, where the targeting moiety TC and the linking alkyl and $X^1$ are replaced by a polylactideglycolide polymer. Compositions and nanoparticles comprising the disclosed compounds are also disclosed herein. Methods of using the disclosed compounds, compositions and nanoparticles to treat various disease states such as cancer or to inhibit cancer cells are also disclosed.

Additional advantages of the disclosed subject matter will be set forth in part in the description that follows, and in part will be obvious from the description, or can be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE FIGURES

The accompanying Figures, which are incorporated in and constitute a part of this specification, illustrate several aspects of the invention and together with the description serve to explain the principles of the invention.

DETAILED DESCRIPTION

Figure 1:
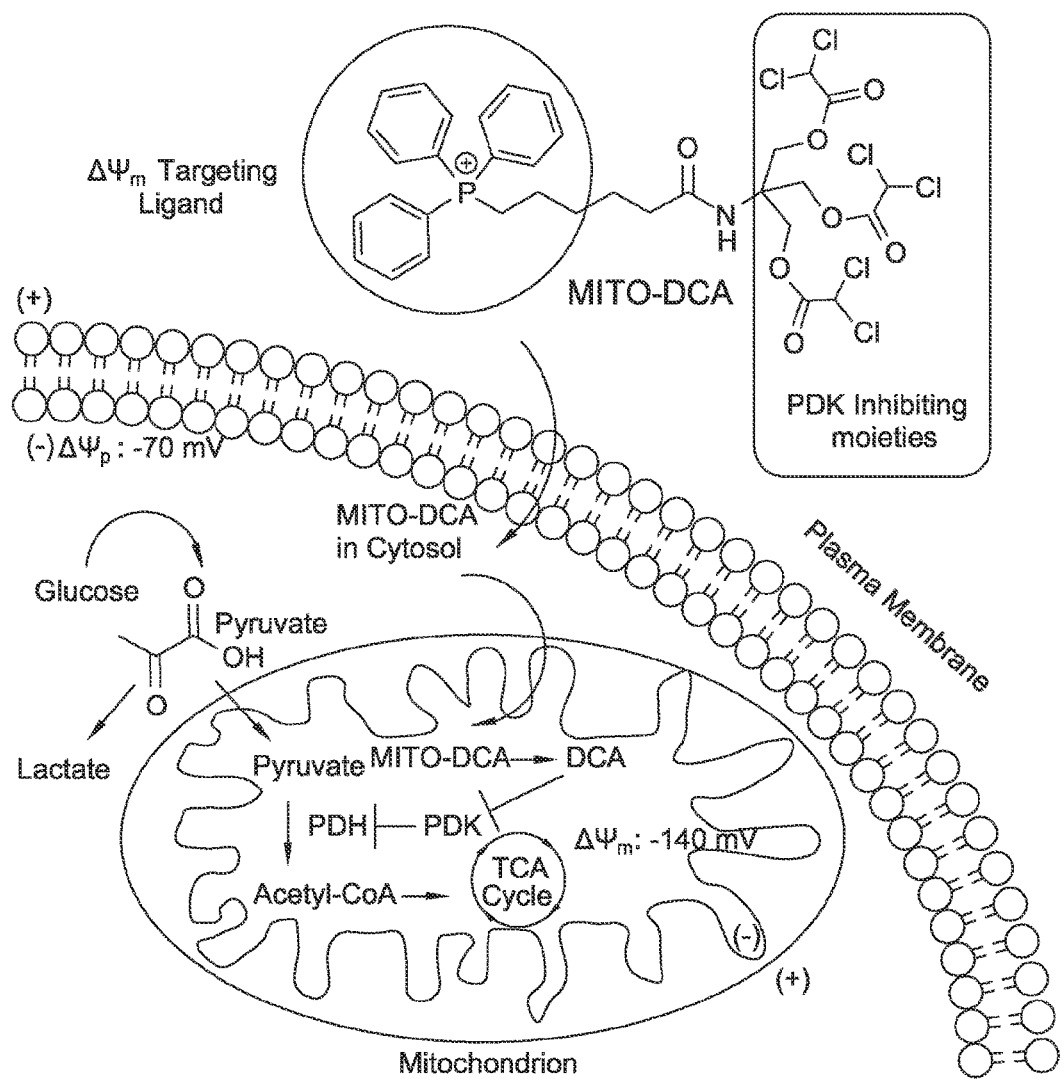
FIG. 1 is a cartoon showing compound MITO-DCA and its mechanism of action.

The compounds, compositions, articles, devices, and methods described herein can be understood more readily by reference to the following detailed description of specific aspects of the disclosed subject matter and the Examples and Figures.

Before the present compounds, compositions, and methods are disclosed and described it is to be understood that the aspects described below are not limited to specific synthetic methods or specific reagents, as such may, of course, vary.

It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

Definitions

In this specification and in the claims that follow, reference will be made to a number of terms, which shall be defined to have the following meanings:

As used in the description and the appended claims, the singular forms "a," "an," and "the" include plural referents unless the context clearly dictates otherwise. Thus, for example, reference to "a composition" includes mixtures of two or more such compositions, reference to "the compound" includes mixtures of two or more such compounds, and the like.

When ranges of values are disclosed, and the notation "from $n_1$ ... to $n_2$" is used, where $n_1$ and $n_2$ are the numbers, then unless otherwise specified, this notation is intended to include the numbers themselves and the range between them. This range can be integral or continuous between and including the end values. By way of example, the range "from 2 to 6 carbons" is intended to include two, three, four, five, and six carbons, since carbons come in integer units. Compare, by way of example, the range "from 1 to 3 µM," which is intended to include 1 µM, 3 µM, and everything in between to any number of significant figures (e.g., 1.255 µM, 2.1 µM, 2.9999 µM, etc.).

The term "about" as used herein is intended to qualify the numerical values which it modifies, denoting such a value as variable within a margin of error. When no particular margin of error, such as a standard deviation to a mean value given in a chart or table of data, is recited, the term "about" should be understood to mean that range which would encompass the recited value itself and the range which would be included by rounding up or down to that figure as well, taking into account significant figures.

By "reduce" or other forms of the word, such as "reducing" or "reduction," is meant lowering of an event or characteristic (e.g., tumor growth). It is understood that this is typically in relation to some standard or expected value, in other words it is relative, but that it is not always necessary for the standard or relative value to be referred to. For example, "reduces tumor growth" means reducing the rate of growth of a tumor relative to a standard or a control.

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed.

As used herein, the terms "treating" and "treatment" refer to delaying the onset of, retarding or reversing the progress of, or alleviating or preventing either the disease or condition to which the term applies, or one or more symptoms of such disease or condition.

The term "individual" (and, equivalently, "subject" or "patient") means all mammals including humans. Examples of individuals include humans, cows, dogs, cats, goats, sheep, pigs, and rabbits. Preferably, the individual is a human.

The term "disease" as used herein is intended to be generally synonymous, and is used interchangeably with, the terms "disorder," "syndrome," and "condition" (as in medical condition), in that all reflect an abnormal condition of an individual (e.g., a human or animal body or of one or more of its parts that impairs normal functioning), is typically manifested by distinguishing signs and symptoms, and/or causes the individual to have a reduced duration or quality of life.

The term "combination therapy" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

As used herein, the term "administering" means oral administration, administration as a suppository, topical contact, intravenous, intraperitoneal, intramuscular, intralesional, intranasal or subcutaneous administration, or the implantation of a slow-release device, e.g., a mini-osmotic pump, to a subject. Administration is by any route including parenteral, and transmucosal (e.g., oral, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, and the like.

The term "therapeutically acceptable" refers to those compounds (or salts, tautomers, zwitterionic forms, etc.) which are suitable for use in contact with the tissues of patients without undue toxicity, irritation, and allergic response, are commensurate with a reasonable benefit/risk ratio, and are effective for their intended use.

Unless stated to the contrary, a formula with chemical bonds shown only as solid lines and not as wedges or dashed lines contemplates each possible isomer, e.g., each enantiomer, diastereomer, and meso compound, and a mixture of isomers, such as a racemic or scalemic mixture.

Reference will now be made in detail to specific aspects of the disclosed materials, compounds, compositions, articles, and methods, examples of which are illustrated in the accompanying Examples and Figures. The examples below are intended to further illustrate certain aspects of the methods and compounds described herein, and are not intended to limit the scope of the claims.

Methods and Compositions

Disclosed herein are compounds that contain a mitochondria targeting moiety and a therapeutic agent moiety linked together by a linker moiety. The therapeutic agent moieties disclosed herein are inhibitor moieties (IM). In one aspect, the disclosed compounds can be represented by Formula I:

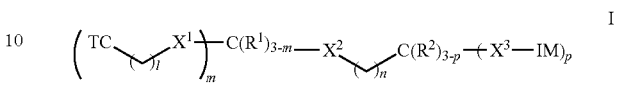

where "TC" is a mitochondria targeting moiety and "IM" is an inhibitor moiety. In Formula I, l is from 1 to 10; m is from 1 to 3; n is from 0 to 20; p is from 1 to 64, preferably 1-3; $X^1$ is —$CO_2$—, —$CO_2CH_2$—, —$CONR^3$—, —$SO_2NR^3$—, —$CHR^3$—, —$NHR^3$—, —CO—, or —O—; $X^2$ is —$CONR^3$—, —$SO_2NR^3$, —$CHR^3$—, —$NHR^3$—, —CO—, or —O—; $X^3$ is a suitable linker depending on the available site on the particular inhibitor of interest, e.g., $X^3$ is —$CO_2$—, —OC(O)—, —$NHR^3$—, —$SO_2$—, —CO—, —S—, —O—, -1,2,3-triazole-; and $R^1$, $R^2$, and $R^3$ are, independently of one another, —H, —F, —Cl, —Br, —OH, —$C_{1-6}$ alkyl, or —OC(O)$C_{1-6}$ alkyl. Pharmaceutically acceptable salts of compounds having Formula I are also disclosed.

In certain examples of Formula I, m is 1, 2, or 3, $X^1$ is —$CO_2$— or —$CHR^3$—; $X^2$ is —$CONR^3$—, —$SO_2NR^3$—, —$CHR^3$—, —$NHR^3$—, —CO—, or —O—, preferably, —$CONR^3$—; $X^3$ is —$CO_2$—; and $R^1$, $R^2$, and $R^3$ are each —H; p is 1; l is 1 to 5; and n is 0 to 3. In other examples, p is 1, 2, or 3, $X^1$ is —$CO_2$— or —$CHR^3$—; $X^2$ is —$CONR^3$—, —$SO_2NR^3$—, —$CHR^3$—, —$NHR^3$—, —CO—, or —O—, preferably, —$CONR^3$—; $X^3$ is —$CO_2$—; and $R^1$, $R^2$, and $R^3$ are each —H; m is 1; l is 1 to 5; and n is 0 to 3.

As noted above, $X^3$ can be a 1,2,3-triazole, which is formed by a 1,3-dipolar cycloaddition reaction between azide and alkyne moieties on an inhibitor.

In yet another example, the compounds disclosed herein can have Formula VI:

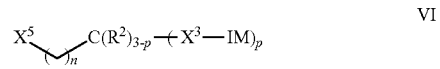

where n, p, IM $R^2$ are as defined herein, and $X^5$ is a polylactide glycolide polymer.

Mitochondria Targeting Moiety ("TC")

"TC" in the formulas disclosed herein is a moiety that targets the mitochondria by selectively delivering the compound to or accumulating the compound in the mitochondria. Exemplary mitochondria targeting moieties ("TC") that can be incorporated into the disclosed compounds are delocalized lipophilic cations, which are effective at crossing the hydrophobic membranes and accumulating in the mitochondria. Triphenylphosphonium (denoted TPP or $(Ph)_3P^+$) containing compounds can accumulate greater than 10 fold within the mitochondria matrix. Any therapeutically acceptable TPP-containing compound can be used as the mitochondria targeting moiety TC in the disclosed compounds. Another delocalized lipophilic cation that can be used as TC in the disclosed compounds are dequalinium.

In other examples, the mitochondria targeting moiety can be a rhodamine cation such as Rhodamine 123 as shown below:

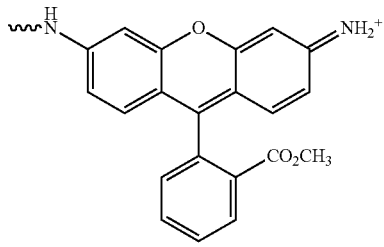

where the secondary amine (as depicted) can be bound to the remainder of the compound shown in Formula I. Rhodamine 6G can also be used.

Non cationic compounds can serve to target and accumulate the disclosed compounds in the mitochondria matrix. For example, Szeto-Shiller peptides can serve as suitable mitochondria targeting moieties in the disclosed compounds to target and accumulate the inhibitor in the mitochondria matrix. Any suitable Szeto-Shiller peptide can be used in the disclosed compounds. Non limiting examples include SS-02 SS-20, and SS-31.

Still further examples of a mitochondria targeting moiety that can be used herein are cyanine dyes such as MKT-123, PK11195, and anthracyclines.

Inhibitor Moiety ("IM")

"IM" in the formulas disclosed herein is a moiety that is an inhibitor or therapeutic agent when attached to the disclosed compounds or when free (i.e., when cleaved from the disclosed compounds). Exemplary inhibitors that can be incorporated into the disclosed compounds include mitochondrial acting anti-cancer agents. For example, the inhibitor IM can be a modulator of the BCL-3 protein family, such as compounds that act on $BCL-X_L$, BCL-2, BCL-1, MCL1, or the like; compounds that affect HK, affect HK2-VDAC interaction, PDK inhibitors, affect LDH-A, affect fatty acid synthase, affect ATP citrate lyase, acetyl-CoA carboxylase inhibitors, or the like; VDAC-targeting or ANT-targeting agents; ROS regulators such as SOD inhibitors, GSH inhibitors, GPX inhibitors or the like; HSP90 inhibitor or the like. Examples of specific inhibitors IM that can be present in the disclosed compounds include lonidamine, dichloroacetate, alpha-tocopheryl succinate, methyl jasmonate, betulinic acid, and resveratrol, A-385358, ABT-263, ABT-737, AT-101, 2-amino-6-bromo-4-(1-cyano-2-ethoxy-2-oxoethyl)-4H-chromene-3-carboxylate (HA14-1), LDH-A shRNA, orlistat, SB-204990, soraphen A, 4-(N-(s-glutathionylacetate)aminophenylarsenoxide (GSAO), clodronate, PK11195, menadione, beta-lapachone, CD437, gamitrinibs, 8-(2-chloro-3,4,5-trimethoxybenzyl)-2-fluoro-9-(pent-4-nyl)-9H-purin-6-amine (PU24FCl), (8-(6-bromobenzo[d][1,3,]dioxyl-5-ylthio)-9-(pent-4-nyl)-9H-purin-6-amine (PUH58), 8-(6-iodobenzo[d][1,3,]dioxyl-5-ylthio)-9-(3-isopropylamino)propyl-9H-purin-6-amine (PUH71), shepherdin, 2-methoxyestradiol, tetrathiomolybdate, buthionine sulphoximine, dimethylamino-parthenolide, parthenolide, imexons, magafodipir, menadione, motexafin gadolinium, PEITCs, elescomol (STA-4783), all trans-retinoic acid, 6-[3-(1-adamantyl)-4-hydroxyphenyl]-2-naphthalene carboxylic acid, E-3-(4'-hydroxy-3'-adamantylbiphenyl-4yl)acrylic acid, 3-bromopyruvate, butyric acid, 2-deoxyD-glucose, arsenite trioxide, betulinic acid and the like.

In certain examples, the inhibitor moiety IM is a Bcl-2 inhibitor, such as oblimersen sodium, AT-101, ABT-263, GX15-070, gossypol, TW-37, ApoG2, ABT 737, and obatoclax.

DCA

In one aspect, the disclosed compounds are engineered for efficient DCA cellular and mitochondrial uptake to induce anticancer activity. The disclosed compounds can also enhance the effects of anti-tumor immunity at pharmacologically relevant doses. For DCA, the disclosed compounds can be particularly advantageous.

DCA encounters tremendous barriers in its navigation to enter the mitochondria. The monocarboxylate transporters which are linked to DCA cellular entry are electroneutral in most cells including tumor (Jackson et al., *J. Biol. Chem.* 271:861-868, 1996). Lactate, pyruvate, and ketone bodies are natural substrates for this transport system; hence DCA faces strong competition with these substrates for its uptake. Moreover, for mitochondrial uptake, DCA competes with pyruvate for its entry via the mitochondrial pyruvate transporter. Studies identified a new sodium-coupled monocarboxylate transporter (SMCT1) or solute carrier family-5 member-8 (SLC5A8), which is linked in the transport of acetate, propionate, butyrate, lactate, pyruvate, 3-bromopyruvate, nicotinate, and evidenced that this highly energy-coupled transporter would accept DCA as a substrate. (Coady et al., *J. Physiol.* 557:719-731, 2004; Miyauchi et al., *J. Biol. Chem.* 279:13293-13296, 2004.) However, this transporter is expressed in normal cells, but expression is silenced in tumor cells. (Li et al., *Proc. Natl. Acad. Sci. USA* 100:8412-8417, 2003; Babu et al., *Oncogene* 30:4026-4037, 2011.) Thus the lack of SLC5A8 makes tumor cells resistant to the anti-tumor activity of DCA. Lactate is the most abundant product of highly glycolytic tumor and some of the effects of high levels of extracellular lactate include: blocking of monocyte differentiation to dendritic cells (DCs), significant inhibition of cytokine release from DCs and cytotoxic T lymphocytes, inhibition of monocyte migration, and reduction of cytotoxic T-cell function (Gottfried et al., *Blood* 107:2013-2021, 2006). Inhibition of glycolysis using DCA can overcome immune suppressive nature of glycolytic tumor; however, it needs very high DCA doses.

Taking advantage of the fact that cancer cells frequently have more negatively charged mitochondria, disclosed herein is a way to circumvent low efficacy by targeted delivery of DCA using a lipophilic mitochondria targeting moiety, e.g., triphenylpohsphonium (TPP) cation, which equilibrates across the membranes in a Nernstian fashion and accumulates into the mitochondrial matrix space in inverse proportion to $\Delta\psi_m$ (FIG. 1). (Smith et al., *Proc. Natl. Acad. Sci. USA* 100:5407-5412, 2003; Ross et al., *Biochem. J.* 411:633-645, 2008; Marrache et al., *Proc. Natl. Acad. Sci. USA* 109:16288-16293, 2012; Marrache et al., *Proc. Natl. Acad. Sci. USA,* 2013.) Thus, disclosed herein, in one aspect is a technology for construction of a mitochondria targeted DCA analogue, e.g., MITO-DCA, by incorporating a targeting moiety (e.g., TPP moiety) (e.g., FIG. 1), its ability to alter cancer cell metabolism to improve the immune status modulated by lactic acid and to increase the effectiveness of anti-tumor immunity.

Making reference to Formula I, compound MITO-DCA (shown in FIG. 1) is when TC=triphenylphosphonium, IM=DCA, 1 is 3, $X^1$ is —CHR$^1$—, m is 1, $R^1$, $R^2$, and $R^3$ are all H, $X^2$ is —CONR$^1$—, n is 0, p is 3, and $X^3$ is $CH_2$. Further analogs containing the triphenylphosphonium targeting moiety and DCA inhibitor are disclosed herein and are shown in Formula II:

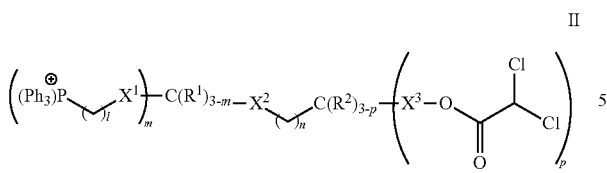

where l is from 1 to 10; m is from 1 to 3; n is from 0 to 20; p is from 1 to 64, preferably 1-3; $X^1$ is —$CO_2$—, —$CO_2CH_2$—, —$CONR^3$—, —$SO_2NR^3$—, —$CHR^3$—, —$NHR^3$—, —CO—, or —O—; $X^2$ is —$CONR^3$—, —$SO_2NR^3$—, —$CHR^3$—, —$NHR^3$—, —CO—, or —O—; and $R^1$, $R^2$, and $R^3$ are, independently of one another, —H, —F, —Cl, —Br, —OH, —$C_{1-6}$ alkyl, or —$OC(O)C_{1-6}$ alkyl. Pharmaceutically acceptable salts of compounds having Formula II are also disclosed.

In certain examples of Formula II, m is 1, 2, or 3, $X^L$ is —$CO_2$— or —$CHR^3$— and $X^2$ is —$CONR^3$—, —$SO_2NR^3$—, —$CHR^3$—, —$NHR^3$—, —CO—, or —O—, preferably, —$CONR^3$—; and $R^1$, $R^2$, and $R^3$ are each —H; p is 1; l is 1 to 5; and n is 0 to 3. In other examples, p is 1, 2, or 3, $X^1$ is —$CO_2$— or —$CHR^3$— and $X^2$ is —$CONR^3$—, —$SO_2NR^3$—, —$CHR^3$—, —$NHR^3$—, —CO—, or —O—, preferably, —$CONR^3$—; and $R^1$, $R^2$, and $R^3$ are each —H; m is 1; l is 1 to 5; and n is 0 to 3. In still further examples, m is 1, 2, or 3, $X^1$ is —$CH_2$— and $X^2$ is —CONH—, and $R^1$ and $R^2$ are each —H; p is 1; l is 1 to 3; and n is 0. In still further examples, p is 1, 2, or 3, $X^1$ is —$CH_2$— and $X^2$ is —CONH—, and $R^1$ and $R^2$ are each —H; m is 1; l is 1 to 3; and n is 0.

In another example, the compounds disclosed herein have Formula III:

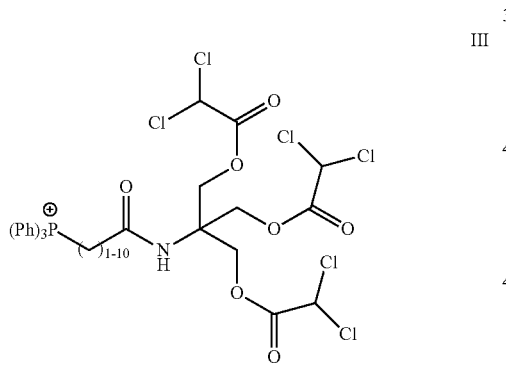

In still other examples, the disclosed compounds can have formula IV or V.

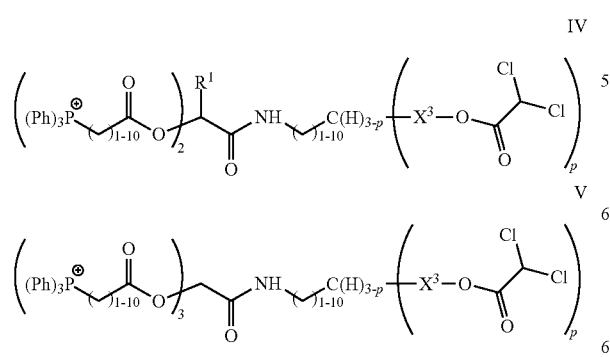

where p is 1 to 64, preferably 1-3, and $R^1$ is $C_{1-3}$ alkyl or H.

In further examples the compound is

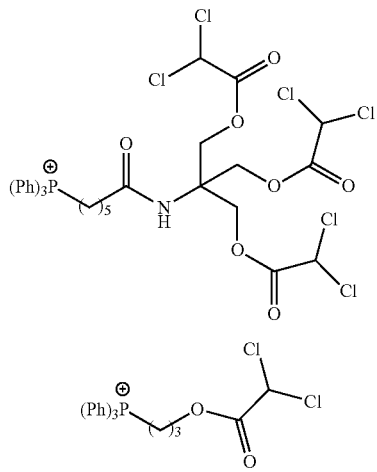

or a pharmaceutically acceptable salt thereof.

MITO-DCA

Figure 2:
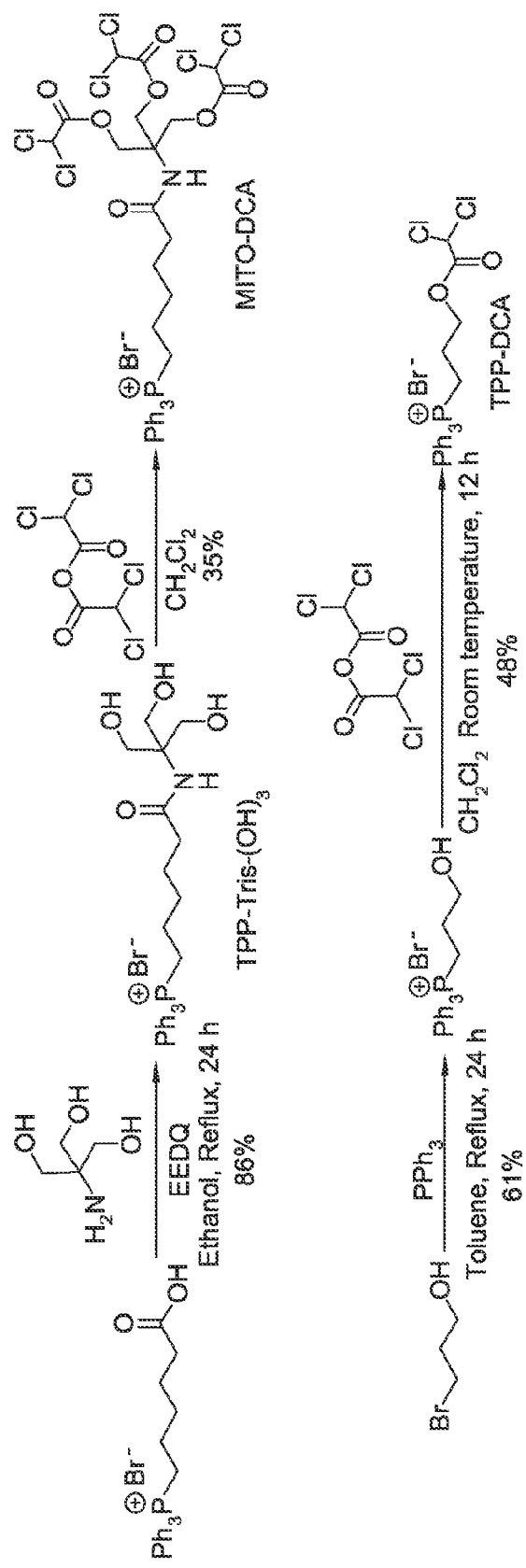
FIG. 2 is a scheme showing the chemical synthesis of two mitochondria-targeted DCA analogues, MITO-DCA and TPP-DCA.

DCA mediated inactivation of PDK1 kinase activity requires DCA to be bound with the N-terminal helix bundle of PDK (Kato et al., *Structure* 15:992-1004, 2007). Such a binding causes local conformational changes in PDK1, which communicate to both nucleotide-binding and lipoyl-binding pockets leading to inhibition of kinase activity. MITO-DCA can be activated by the esterases present in the mitochondria to release the active drug for its accumulation in the PDK1 binding pocket. In MITO-DCA, the mitochondria targeting TPP cation is introduced via an amide linkage and multiple DCA molecules were incorporated via tris (hydroxymethyl)aminomethane (Tris) using esterase-labile ester bonds (Dhar et al., *J. Am. Chem. Soc.* 129:8702-8703, 2007). This design can allow release of DCA molecules in an esterase-dependent manner under physiological conditions for effective PDK1 binding without having any steric encumbrance from the bulky TPP moiety and the use of the comparatively stable amide linkage for TPP conjugation will allow us to direct MITO-DCA to the mitochondria (FIG. 1) avoiding any premature detachment of the targeting moiety from DCA before reaching the mitochondria of cells. To construct MITO-DCA, TPP-Tris-$(OH)_3$ is first synthesized by reacting (5-carboxypentyl)triphenylphosphonium bromide with Tris using N-ethoxycarbonyl-2-ethoxy-1,2-dihydroquinoline (EEDQ), a highly specific reagent that enables the coupling of amine with carboxyl in the presence of hydroxyl groups (FIG. 2). The hydroxyl groups from TPP-Tris-$(OH)_3$ are coupled with DCA-anhydride to result MITO-DCA. Coupling other inhibitors IM to the TPP-Tris-$(OH)_3$ intermediate can be accomplished in a similar manner.

MITO-DCA contains three DCA moieties per TPP molecule, allowing the delivery of higher DCA dose using one targeting ligand. This can translate to increased therapeutic benefit. Thus, MITO-DCA has the potential to deliver more drug dose using a single TPP targeting moiety. Similar delivery efficiency can be expected with the other inhibitors IM disclosed herein.

Also disclosed is TPP-DCA, which contains one DCA per TPP molecule. TPP-DCA is synthesized by reacting (3-hydroxypropyl)triphenylphosphonium bromide with DCA-anhydride as shown in FIG. 2. Other inhibitors IM can be attached in a similar manner.

Mitochondrial Membrane Potential and MITO-DCA

Figure 3:
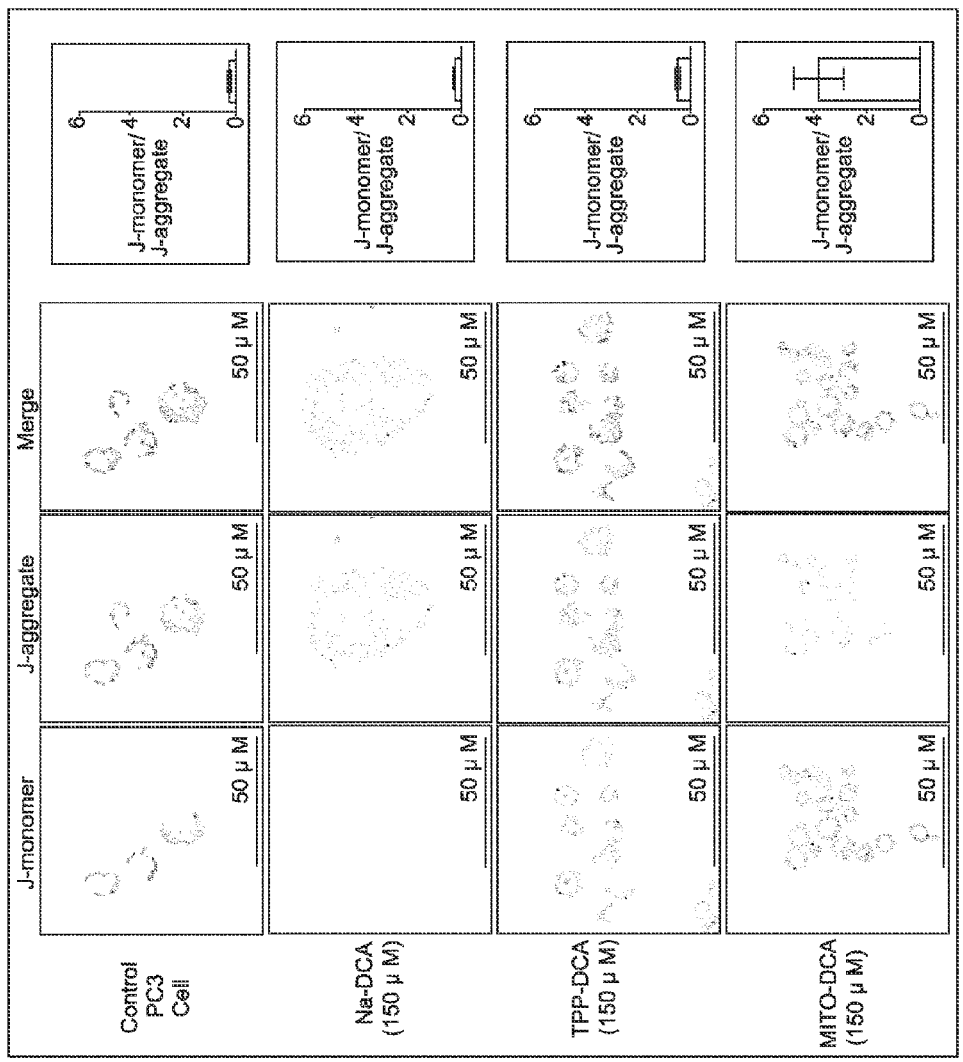
FIG. 3 is a collection of images showing the changes in the $\Delta\psi_m$ by the JC-1 assay. The figure shows that treatment of PC3 cells with 50 μM MITO-DCA dramatically caused the collapse of $\Delta\psi_m$ in these cells compared to Na-DCA or TPP-DCA. Cells were stained with JC-1 for 15 min. Green fluorescence, depolarized (J-monomer) mitochondria; red fluorescence, hyperpolarized (J-aggregates). The shift in membrane potential observed by disappearance of red-orange-stained mitochondria (large negative $\Delta\psi_m$) and an increase in fluorescent green-stained mitochondria (loss of $\Delta\psi_m$) by MITO-DCA is higher compared that observed by TPP-DCA or Na-DCA. The JC-1 green/red ratio results from the mitochondria in all four groups are shown in the right.

An early indication of the initiation of cellular apoptosis is the collapse in the electrochemical gradient across the mitochondrial membrane, as measured by the change in the $\Delta\psi_m$ (Perry et al., *BioTechniques* 50:98-115, 2011). Loss of mitochondrial $\Delta\psi_m$ can be studied using a unique cationic dye, 5,5',6,6'-tetrachloro-1,1',3,3'-tetraethylbenzimidazolylcarbocyanine iodide or JC-1 that exhibits potential-dependent accumulation in the mitochondria accompanied by a fluorescence emission shift from green (525 nm) to red (590 nm). The potential-sensitive color shift is due to the concentration dependent formation of red fluorescent "J aggregates." Mitochondrial depolarization is indicated by an increase in the green/red fluorescence intensity ratio. Live cell imaging of prostate cancer (PCa) PC3 cells treated with Na-DCA (150 µM), TPP-DCA (150 µM), or MITO-DCA (50 µM), followed by staining with JC-1, and a comparative analysis of the JC-1 green/red fluorescence ratio from PC3 cells in response to these three DCA analogues are represented in FIG. 3. Exposure of PC3 cells to MITO-DCA induced marked changes in $\Delta\psi_m$ as evident from the disappearance of red fluorescence and the increase of green fluorescence in most cells. In contrast, cell treatment with Na-DCA or TPP-DCA showed red fluorescence in most cells. Quantification of fluorescence intensities was carried out using ImageJ and the corrected total cell fluorescence (CTCF) values are represented as histograms (FIG. 3). Quantitative analysis of JC-1-stained PC3 cells revealed a significant decrease in the red (high $\Delta\psi_m$) to green (low $\Delta\psi_m$) ratio in MITO-DCA (Green:Red; 3.96±0.96) treated cells compared with control cells (Green:Red; 0.24±0.03), or the cells which were treated with Na-DCA (Green:Red; 0.24±0.02) at an equivalent DCA concentration. TPP-DCA showed a green:red ratio of 0.49±0.09 which was significantly lower than the ratio showed by MITO-DCA. The ability of MITO-DCA to cause reduction in $\Delta\psi_m$ in a highly glycolytic PC3 cells at a concentration such as 50 µM indicates that incorporation of mitochondria targeting moiety and loading of multiple DCA units in a single molecule can help overcome the problems associated with high dosage required for Na-DCA to show its efficacy.

MITO-DCA is More Effective in Highly Glycolytic Cancer Cells

Figure 4:
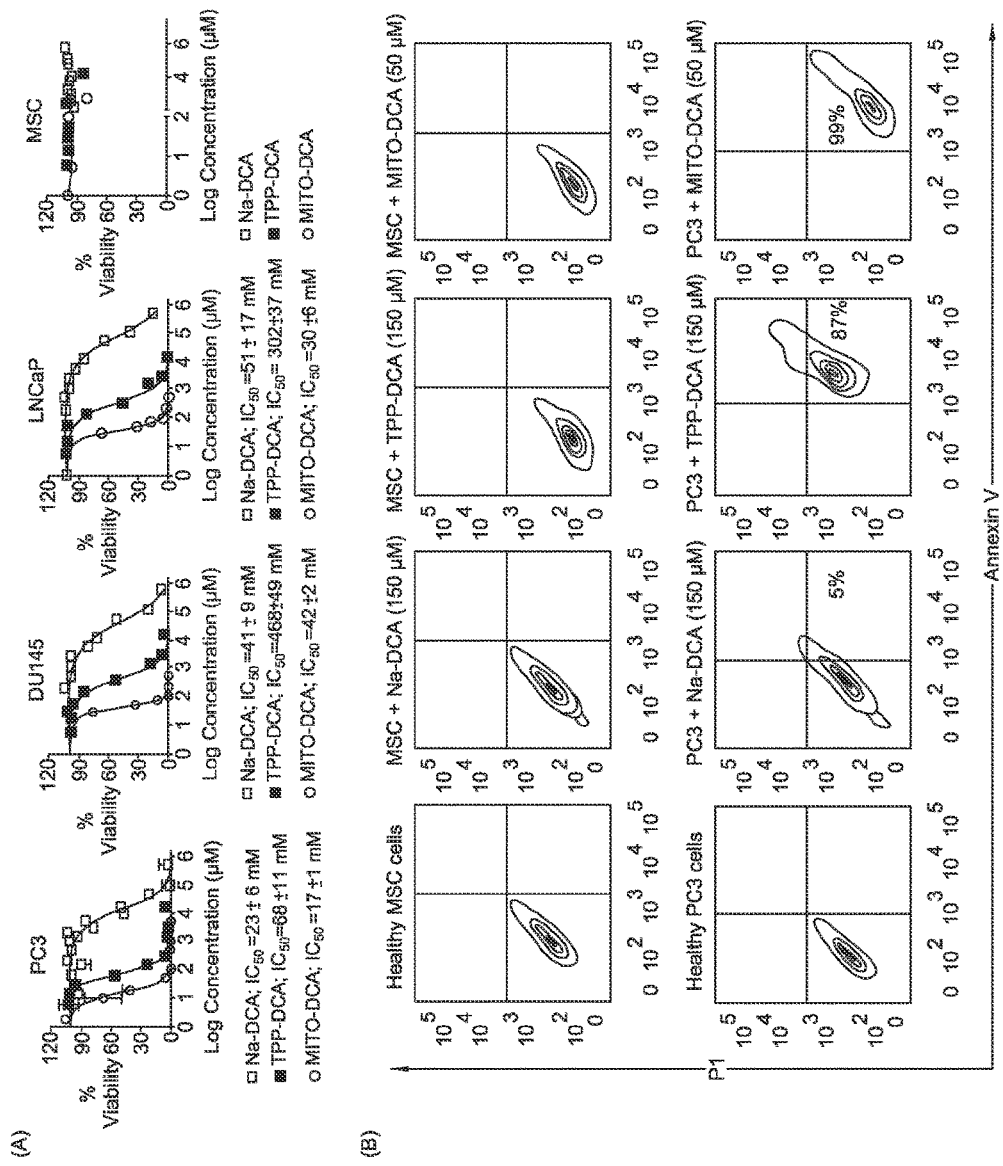
FIG. 4 is a collection of graphs that show efficient selective induction of apoptosis in cancer cells by MITO-DCA. Panel A shows that highly glycolytic PCa PC3 and DU145 cells respond differently to MITO-DCA compared to less glycolytic PCa LNCaP cells; MITO-DCA, TPP-DCA, and Na-DCA have no toxicity in hMSC cells. Cells on 96-well plates were varied concentrations of MITO-DCA, TPP-DCA, and Na-DCA for 12 h and viability was assessed by the MTT assay. A representative experimental data are shown in the figure and the $IC_{50}$ values were calculated from three independent experiments. Panel B shows data from FACS analysis using annexin V-alexa fluor/PI staining for apoptosis detection in MSC and PC3 cells on treatment with MITO-DCA (50 µM), TPP-DCA (150 µM), and Na-DCA (150 µM) for 16 h. Cells in the lower right quadrant indicate annexin-positive/PI negative, early apoptotic cells. The cells in the upper right quadrant indicate annexin-positive/PI positive, late apoptotic or necrotic cells.

Amplified glucose consumption and energy production from glycolysis are basic characteristics of most malignant cells; however, PCa is characterized by a slow glycolysis. Despite unique metabolic features of PCa cells, the glycolytic profiles in androgen-dependent and androgen-independent stages are not well understood (Benedettini et al., *Diagn. Histopathol.* 14:195-201, 2008). The metabolic switching ability of MITO-DCA on different PCa cell types was investigated. Androgen-responsive LNCaP and androgen-nonresponsive PC3 and DU145 PCa cells were used. The metabolic phenotype of LNCaP cells differed from that of DU145 and PC3 cells; LNCaP cells had a significantly greater oxygen consumption rate as well as a significantly lower rate of lactate production. (Id.; Higgins et al., *Biochim. Biophys. Acta* 1787:1433-1443, 2009.) Mesenchymal precursor cells are believed to be the origin for various types of sarcoma and the transformation of these stem cells is a prerequisite for the development of most human malignancies (Helman et al., *Nat. Rev. Cancer* 3:685-694, 2003). Moreover, undifferentiated MSC cells are more glycolytic than primary human fibroblasts and differentiated cells. Human mesenchymal stem cells (hMSC) were therefore used as controls to examine the toxicity profile of MITO-DCA on normal cells. A representative viability assay for MITO-DCA, TPP-DCA, and Na-DCA in PC3, DU145, LNCaP, and MSC cells is shown in FIG. 4A. The cytotoxicity profiles of TPP-Tris-(OH)$_3$, the carrier for targeted delivery of DCA to the mitochondria of cells, revealed that the carrier did not show any toxic effects in any of the PCa or MSC cells. Results indicated that after 72 h incubation, Na-DCA is relatively inactive in all the three PCa cell lines irrespective of their glycolytic states, with IC$_{50}$ values ranging from 20-40 mM in highly glycolytic PC3 and DU145 cells to >50 mM in less glycolytic LNCaP cells (IC$_{50}$(PC3): 23±6 mM; IC$_{50}$(DU145): 41±9 mM; IC$_{50}$(LNCaP): 51±17 mM), and no toxicity was observed in MSC cells. In contrast, when multiple DCA molecules were delivered directly to the mitochondria using a single TPP moiety in the form of MITO-DCA, a remarkable increase in the cytotoxicity in all the three PCa cell lines was observed. MITO-DCA with IC$_{50}$ value of 17±1 µM was found to be three orders of magnitude more active in highly glycolytic PC3 cells. Similar trends were observed in DU145 (IC$_{50}$: 42±2 µM) and LNCaP (IC$_{50}$: 30±6 µM) cells, MITO-DCA showed three orders of magnitude more activity than Na-DCA. TPP-DCA [IC$_{50}$(PC3): 68±1 µM; IC$_{50}$(DU145): 468±49 µM; IC$_{50}$(LNCaP): 302±37 µM] in PC3 cells was ~4 times and in LNCaP and DU145~10 times less active than MITO-DCA. In MSC cells, both MITO-DCA and TPP-DCA did not show any toxic effects at these concentrations demonstrating their unique selectivity to cancer cells.

In order to determine whether the enhanced activity of MITO-DCA upon targeting this compound to the mitochondria of cells was due to apoptosis rather than necrosis, an ALEXA FLUOR™ 488-Annexin-V and propidium iodide (PI) cell staining in PC3 and MSC cells was carried out and data were analyzed using flow cytometry (FIG. 4B). As controls, etoposide treated cells were used as early apoptosis population and $H_2O_2$ treated cells were marked as late apoptotic or necrotic population. The MSC cells did not undergo apoptosis with MITO-DCA (50 µM) or TPP-DCA (150 µM), or Na-DCA (150 µM) treatment. However, at a low concentration of MITO-DCA of 50 µM, complete early apoptosis was observed in PC3 cells; TPP-DCA showed similar behavior at 150 µM, no apoptosis was detected with Na-DCA at a concentration of 150 µM. There were no late apoptotic or necrotic cells observed with these compounds.

Cancer Cell Selective Glucose Metabolism Alteration by MITO-DCA

Figure 5:
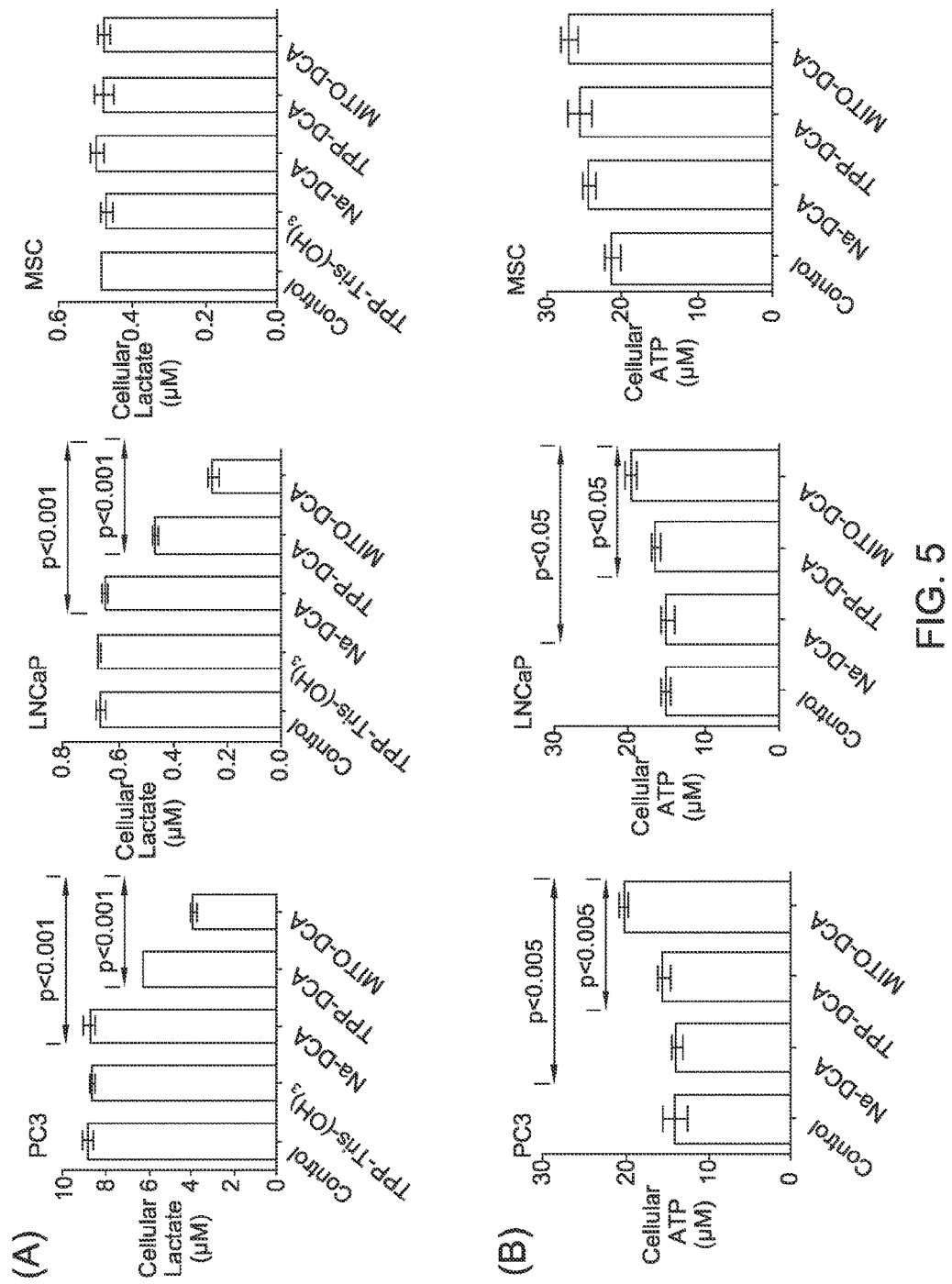
FIG. 5 is a collection of graphs that show MITO-DCA induced alteration of PCa cell metabolism. Panel A shows intracellular lactate levels in PC3, LNCaP, and MSC cells after treatment with 150 µM Na-DCA, 150 µM TPP-DCA, and 50 µM MITO-DCA for 6 h at 37° C. Panel B shows changes in intracellular ATP content associated with the lactate fluctuation in the PC3, LNCaP, and MSC cells after treatment with 60 µM Na-DCA, 60 µM TPP-DCA, and 20 µM MITO-DCA for 3 h at 37° C.

Cytosolic metabolism of glucose to pyruvate occurs before its entry into mitochondria for oxidative phosphorylation. However, if not metabolized through oxidative phosphorylation as found in cancer, pyruvate gets converted by lactate dehydrogenase through glycolysis to lactate. Glycolysis in the absence of oxidative phosphorylation in cancer causes rise in lactate concentration. To test the ability of MITO-DCA to switch glucose metabolism from glycolysis to oxidative phosphorylation in cancer cells, intracellular lactate levels in glycolytic PC3 cells were measured and compared the value with those observed in less glycolytic LNCaP and normal MSC cells (FIG. 5A). To understand the importance of mitochondria targeting ligand and to explore the importance of a Tris platform to increase number of DCA molecule per targeting ligand, the parent drug Na-DCA and TPP-DCA were used as controls. Treatment of PC3 cells with 50 µM of MITO-DCA for 6 h reduced the intracellular lactate levels by 58±5%. Cells treated with the control delivery scaffold TPP-Tris-(OH)$_3$ did not show any effect. PC3 cells treated with 150 µM of Na-DCA showed a reduction in lactate levels by ~5%. TPP-DCA showed less efficiency in reducing cellular lactate levels, the reduction was only by 30±2% (FIG. 5A). As expected, the lactate levels in the less glycolytic LNCaP cells were significantly lower than those observed in PC3 cells. Pronounced lactate concentration differences were observed between healthy glycolytic PC3 and healthy MSC cells (FIG. 5A). The extent of relative decrease in glycolytic activity after treatment with MITO-DCA was similar in PC3 and LNCaP cells and the reduction was much more significant compared to cells treated with TPP-DCA or Na-DCA (FIG. 5A). None of the DCA compounds has any effect on the lactate levels in MSC cells (FIG. 5A). These observations suggest that MITO-DCA is much more efficient in altering the glucose metabolism in cancer cells and it does not show any effect in the normal cells.

Figure 8:
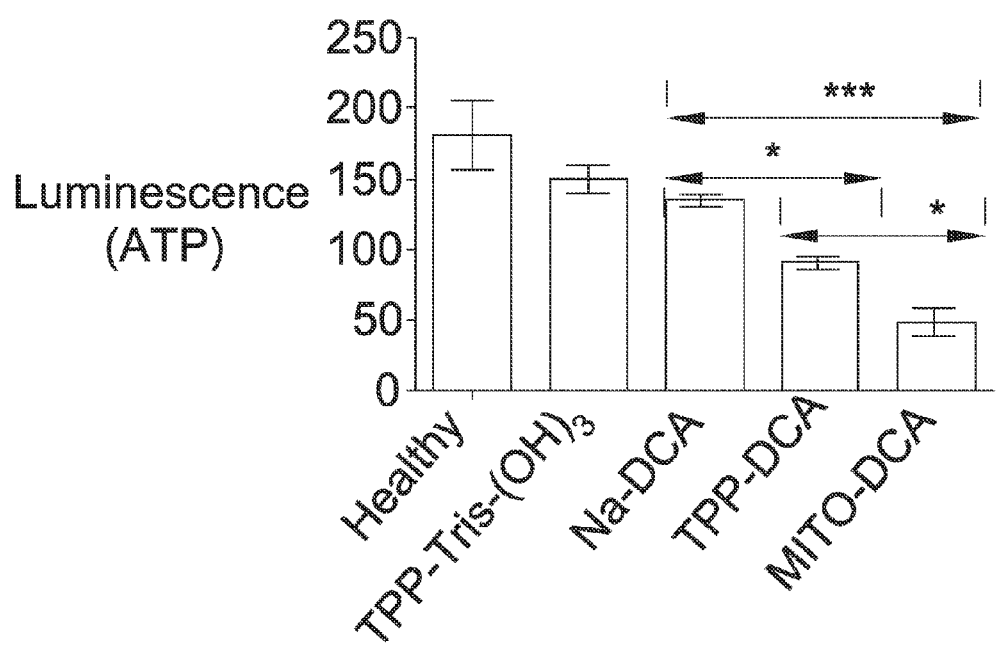
FIG. 8 is a graph showing at high concentrations of the disclosed DCA compounds (MITO-DCA: 50 µM; TPP-DCA; 150 µM; and Na-DCA: 150 µM) with longer incubation time of 6 h, PC3 cells showed ATP reduction and cell growth inhibition.

A decrease in cancer cell lactate levels is expected to be associated with an increase in ATP production. Intracellular ATP levels in PC3, LNCaP, and MSC cells treated with MITO-DCA (20 µM), TPP-DCA (60 µM), and Na-DCA (60 µM) were measured. As shown in FIG. 5B, after 3 h treatment with MITO-DCA, ~44% increase in the intracellular ATP levels was observed. Treatment with TPP-DCA or Na-DCA at three times higher concentrations did not show any significant increase in the intracellular ATP levels. Similar ATP levels were observed in LNCaP cells upon treatment with MITO-DCA, TPP-DCA, and Na-DCA. In contrast, normal MSC cells showed relatively high levels of ATP and upon treatment with all the three DCA compounds, there was marginal increase in the ATP levels. At high concentrations of the DCA compounds (MITO-DCA: 50 µM; TPP-DCA; 150 µM; and Na-DCA: 150 µM) with longer incubation time of 6 h, PC3 cells showed ATP reduction and cell growth inhibition (FIG. 8).

Lactate Reduction by MITO-DCA Results Anti-Tumor Immunity

Figure 6:
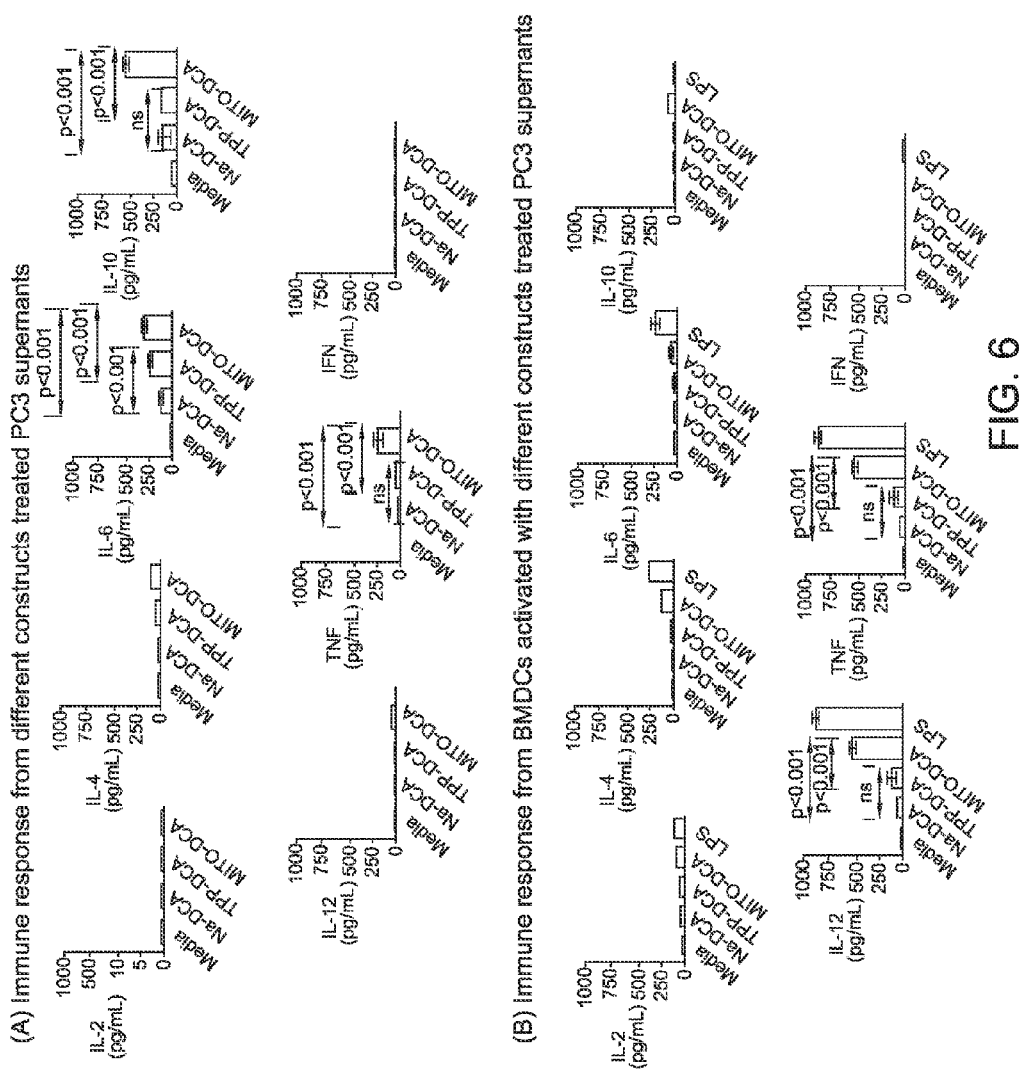
FIG. 6 is a collection of graphs that show lactate reduction by MITO-DCA stimulates anti-tumor immunity. Panel A shows the cytokine production by PC3 cells (0.5×10$^6$ cells/mL) on treatment with MITO-DCA (50 µM), TPP-DCA (150 µM), and Na-DCA (150 µM) for 24 h. Panel B shows that BMDCs activated with supernatants from PC3 cells treated with MITO-DCA, TPP-DCA, and Na-DCA show different cytokine secretion profile from the cancer cell supernatants. BMDCs were cultured at 0.5×10$^6$ cells/mL in the presence of 100 µL of PC3 cancer cell supernatants treated with different constructs. As a control, BMDCs were stimulated with LPS (100 ng/mL). After 24 h, BMDC culture supernatants were harvested and assayed by ELISA to determine the concentrations of IL-2, IL-4, IL-6, IL-10, IL-12, TNF-α, and IFN-γ. All data are expressed as mean±S.D (standard deviation). Statistical analyses were performed using GraphPad Prism software 5.00. A one-way ANOVA with a post-hoc Tukey test was used to identify significant differences among the groups.
Figure 7:
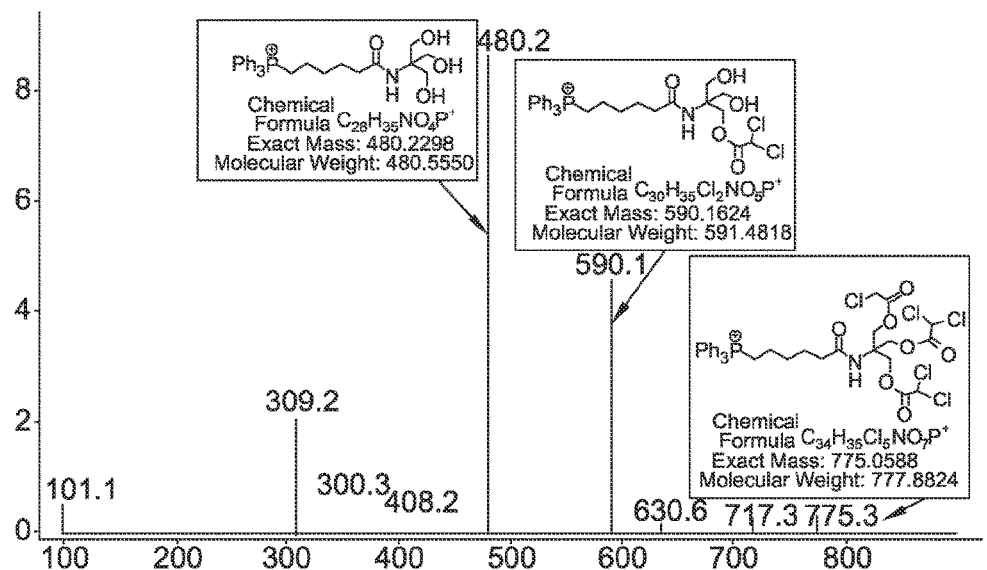
FIG. 7 is a pair of mass spectra, for MITO-DCA (top) and TPP-DCA (bottom), as determined by electrospray ionization mass spectrometry (ESI-MS).
Figure 7:
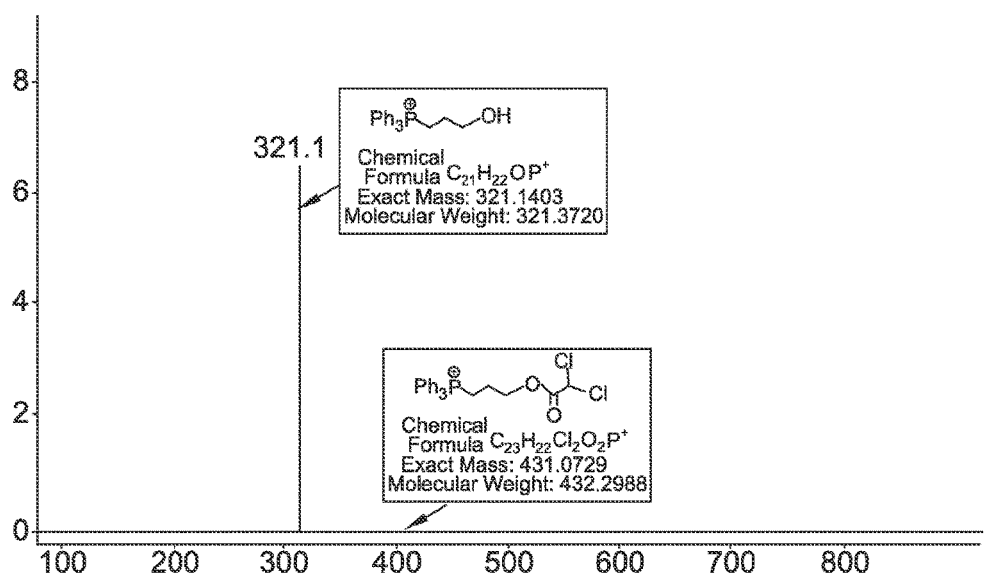

Cancer cells recruit several pathways to evade elimination by the immune system (Kim et al., *Immunology* 121:1-14, 2007). Several mechanisms by which tumor cells escape immunity include upregulation of inhibitory molecules, production of immunosuppressive cytokines, and downregulation of costimulatory molecules (Rabinovich et al., *Annu. Rev. Immunol.* 25:267-296, 2007). Dendritic cells (DCs), the major players for the initiation of a specific anti-tumor T-cell response, are potential target to tumor-mediated immunosuppression. (Gabrilovich et al., *Nat. Med.* 2:1096-1103, 1996; Radmayr et al., *Int. J. Cancer* 63:627-632, 1995; Orsini et al., *Cancer Res.* 63:4497-4506, 2003.) Lactic acid secretion in highly proliferative glycolytic tumor has the ability to induce alteration in antigen phenotype and functional activity of DCs, which contributes to the suppression of local immunity (Gottfried et al. 2006). Tumor derived lactic acid inhibit the differentiation of monocytes to DCs, impair DC activation and antigen expression and suppress the proliferation, cytokine production and cytotoxic activity of T cells (Fischer et al., *Blood* 109:3812-3819, 2007). After observing significant and very selective reduction in lactate levels in PCa cells by MITO-DCA, the impact of the reduced lactate producing PC3 cell supernatants on DCs was investigated. Cancer cell supernatants were generated by treating PC3 cells with MITO-DCA (50 µM), Na-DCA (150 µM), and TPP-DCA (150 µM) for 24 h. First, investigated was the immune responses from the PC3 supernatants upon treatment with different DCA compounds by determining pro-inflammatory and anti-inflammatory cytokines interleukin (IL)-2, IL-4, IL-6, IL-10, IL-12, tumor necrosis factor (TNF)-α, and interferon-gamma (IFN-γ) using enzyme-linked immunosorbent assay (ELISA) (FIG. 6A) (Marrache et al., *Integr. Biol.* 5:215-223, 2013). Treatment of PC3 cells with DCA compounds resulted in up-regulation of IL-6, IL-10, and TNF-α. The levels of all these three cytokines were higher for MITO-DCA treated cells compared to those, which were treated with TPP-DCA or Na-DCA. When DCs are activated appropriately, they take up tumor antigens and apoptotic bodies, migrate to the T-cell-rich area of the lymph nodes, initiate a series of actions for the selection of antigen-specific T cells, and the release of the DC cytokines such as IFN-γ and IL-12. The PC3 supernatants containing the tumor antigens were added to mouse bone marrow derived dendritic cells (BMDCs) and incubated at 37° C. (Marrache et al., 2013). After 24 h incubation, activation of BMDCs by the cancer cell supernatants was studied using ELISA. The BMDCs activated with cancer cell supernatants generated from MITO-DCA showed significant increased secretion of IL-12 (FIG. 6B). TPP-DCA mediated increase in 11-12 from BMDCs was lesser compared to MITO-DCA. Supernatants generated from Na-DCA treatment did not show any increase in IL-12 levels from the BMDCs. MITO-DCA thus has the ability to facilitate the induction of T helper cell type 1 (Th1)-promoting BMDCs by enhancing IL-12 (Lamont et al., *Immunol. Today* 17:214-217, 1996) and reducing IL-10 production. An enhanced IL-12 secretion by MITO-DCA-treated tumor supernatant increases the potential of enhancing natural killer cell and cytotoxic T lymphocyte activities. Acidification by lactic acid results in the suppression of TNF-α secretion by human monocytes and mouse macrophage (Dietl et al., *J. Immunol.* 184:1200-1209, 2010). Our data showed that the cancer cell supernatants generated from the DCA compounds treatment stimulated BMDCs to secret TNF-α and the highest level of this cytokine was observed from the supernatants, which was generated from MITO-DCA due to efficient alteration of glucose metabolism from glycolysis to glucose oxidation. These results support that MITO-DCA would be a better agent for the improvement of anti-tumor immunity compared to the parent drug DCA, altered cytokine pattern in the cancer cells as a result of effective lactate reduction at a low concentration of MITO-DCA has the ability to modulate DC phenotype which may contribute to anti-tumor immunity.

The ability of MITO-DCA to reverse metabolism of PCa with unique metabolism phenotype suggests enormous potential of DCA when it is directed selectively to the mitochondria and warrants for further investigation. The TPP-based ligands represent an important class of the non-peptidic mitochondrial targeting agents, however, prior to this work; this approach was never used for DCA intracellular compartmentalization. The molecular scaffold used in MITO-DCA provides opportunity to incorporate more copies of DCA keeping a single TPP targeting moiety without affecting TPP-related mitochondrial toxicity. The lack of sensitivity of the non-cancerous MSC cells to the clinically relevant concentrations of MITO-DCA suggests that this platform has the potential to be non-toxic in normal tissue. Effective lactate reduction in tumor cells by precise targeting of DCA to the mitochondria of cells in the form of MITO-DCA not only changed the tumor cell glycolysis, but also altered the immune status modulated by lactic acid and increased the anti-tumor immunity. These data suggest that the targeting DCA to the mitochondria can stimulate cancer cell metabolism in unique ways, which can create new strategies for immunogenic DCA therapy. Precise targeting of DCA to the mitochondria of cells in the form of MITO-DCA as demonstrated here can reveal new avenues to provide a novel formulation of this wonder molecule DCA with high efficacy and eliminating the potential sources of toxicity for existing medicines.

Dendrimeric Compounds

Because of their precise architecture, high loading capacity, tunable solubility, and bioconjugation capability, the compounds disclosed herein can comprise dendrimers or hyperbranched polymers with multiple targeting moieties and inhibitors IM. The combination of the unique properties of dendrimers and hyperbranched polymers with the targeting moieties and inhibitor moieties can lead to a more efficient-synthesis of compounds possessing high efficiency, for example, for bulk production.

Suitable dendrimers scaffolds that can be used herein include poly(amidoamine), also known as PAMAM, or STARBURST™ dendrimers; polylysine dendrimers; and polypropylenimine (PPI) dendrimers. The manufacturing process for these dendrimers is a series of repetitive steps starting with a central initiator core (e.g., ethylenediamine-cores). Each subsequent growth step represents a new "generation" of polymer with a larger molecular diameter, twice the number of reactive surface sites, and approximately double the molecular weight of the preceding generation. Dendrimeric scaffolds suitable for use herein are commercially available in a variety of generations. Preferable, the disclosed dendrimeric compounds herein are based generation 0, 1, 2, 3, 4, 5, 6, 7, 8, 9, or 10 dendrimeric scaffolds. Such scaffolds have, respectively, 4, 8, 16, 32, 64, 128, 256, 512, 1024, 2048, and 4096 reactive sites. Thus, the disclosed dendrimeric compounds based on these scaffolds have the corresponding number of combined TC and IM moieties.

Polyether amines are also suitable and contain primary amino groups attached to the terminus of a polyether backbone. The polyether backbone is typically based either on propylene oxide (PO), ethylene oxide (EO), or mixed EO/PO/BO. In one aspect, the polyether amine can be a polyoxyalkyleneamines. Such polyether amines can be obtained commercially from Huntsman Performance Products (Salt Lake City, Utah) under the name JEFFAMINE™ (e.g, JEFFAMINE D230). JEFFAMINES can have mono-amines, diamines, and triamines, and are available in a variety of molecular weights, ranging up to 5,000.

Further examples of suitable dendrimers are based on 2,2-bis(hydroxymethyl)propionic acid (MPA). These hyperbranched polymers are commercially available in 2, 3, or 4, generations, which respectively have 16, 32, and 64 reactive sites for linking the disclosed TC and IM moieties.

Still further, suitable dendrimers can be prepared by combining two or more dendrons. Dendrons are wedge-shaped sections of dendrimers with reactive focal point functional groups. Many dendron scaffolds are commercially available. They come in 1, 2, 3, 4, 5, and $6^{th}$ generations with, respectively, 2, 4, 8, 16, 32, and 64 reactive groups. In certain examples, TC moieties are linked to one type of dendron and the inhibitor moieties are linked to another type of dendron. The two dendrons are then connected to form a dendrimer. A specific example of these compounds is shown below where a $2^{nd}$ generation MPA dendron with 4 reactive sites was coupled to triphenylphosphinyl containing TC moieties. A separate $5^{th}$ generation MPA dendron, with 32 reactive sites, was coupled to DCA. The two dendrons were then linked via click chemistry (i.e., a 1,3-dipolar cycloaddition reaction between an azide moiety on one dendron and alkyne moiety on another to form a triazole linker.

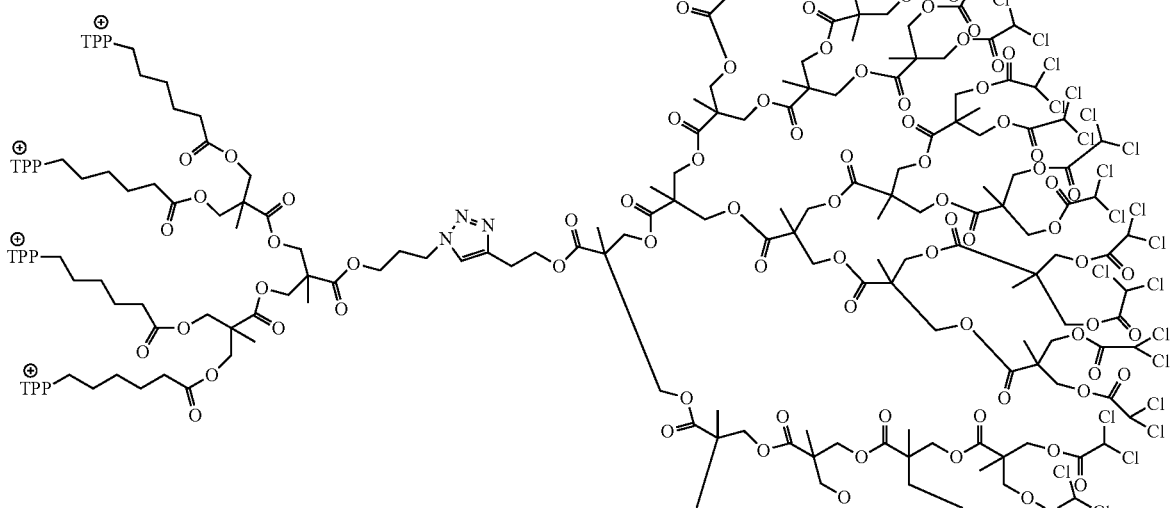

-continued

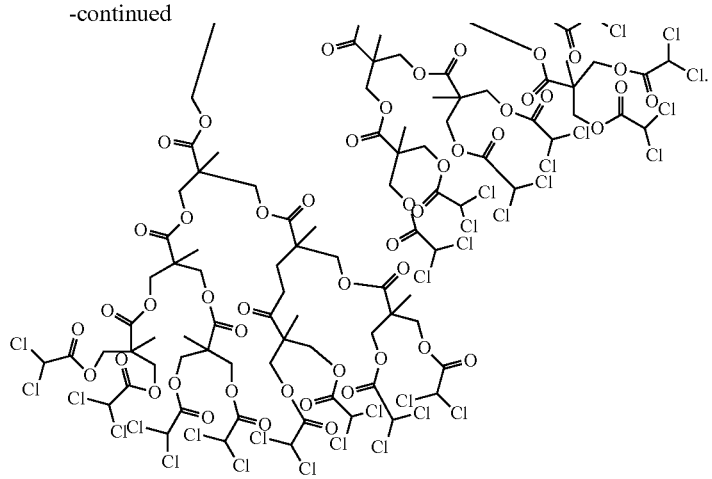

Various permutations of this structure are contemplated herein. For example, suitable dendrimers can contain 2, 4, 8, 16, 32, or 64 TC moieties (e.g., TPP) per 2, 4, 8, 16, 32, or 64 inhibitor moieties (e.g., DCA). The skilled artisan will understand how to select the appropriate generation dendrons for constructing these various combinations and can follow known synthetic methodology for their production, such as is disclosed in Medina et al., Chem. Rev. 2009, 109, 3141-3157 and Tekade et al., Chem. Rev. 2009, 109, 49-87, which are incorporated herein by reference in their entireties for their teachings of dendrimers, hyperbranched polymers, and dendrons.

Further, the linking group between the two dendrons can be varied, e.g., triazoles, amides, thioesters, esters, ethers, disulfides, and the like. A further example of a dendrimer as contemplated herein is shown below where two $4^{th}$ generation dendrons based on MPA, each with 32 reactive groups coupled to either the TC moieties or the inhibitor moieties, were linked together.

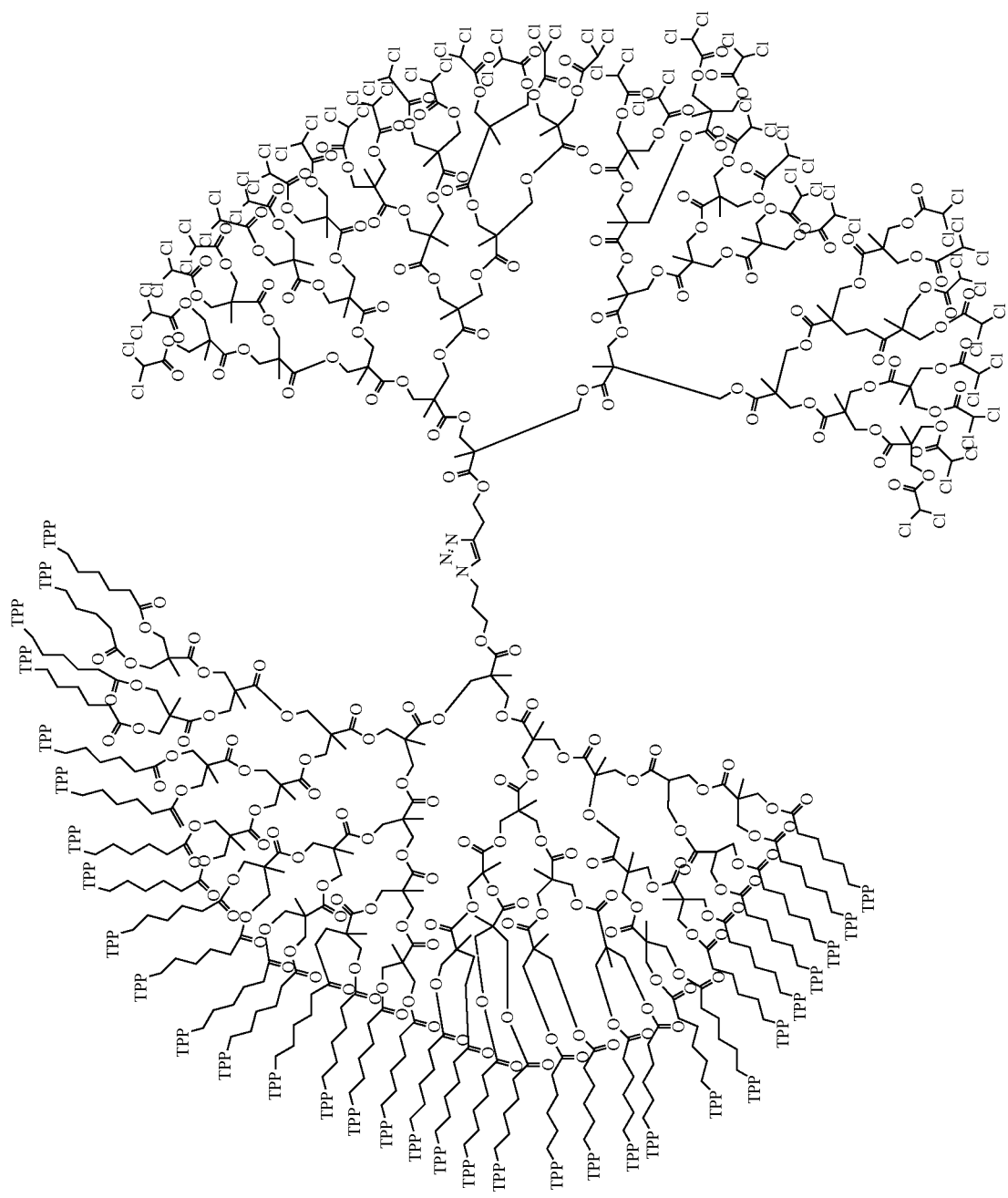

The disclosed compounds can also be based on a hyperbranched polyglycol structure. These hyperbranched polymers can be synthesized in one step by random copolymerization of ethylene oxide and glycidol (Shenoi et al., *Biomaterials* 34 6068-6081, 2013, and Xu et al., *Polym. Chem.*, 4:3480-3490, 2013, which are incorporated herein by reference in their entireties for their teachings of dendrimers, hyperbranched polymers, and dendrons). A specific example of these compounds is shown below.

interaction with the cellular components, which interactions will target the nanoparticles to the appropriate cells, such as apoptotic cells; organelles, such as mitochondria; or the like.

The core of the nanoparticle can be formed from any suitable component or components. Preferably, the core is formed from hydrophobic components such as hydrophobic polymers or hydrophobic portions or polymers or lipids. In certain examples, the core includes phospholipids which can form micelles having a hydrophobic core and a hydrophilic

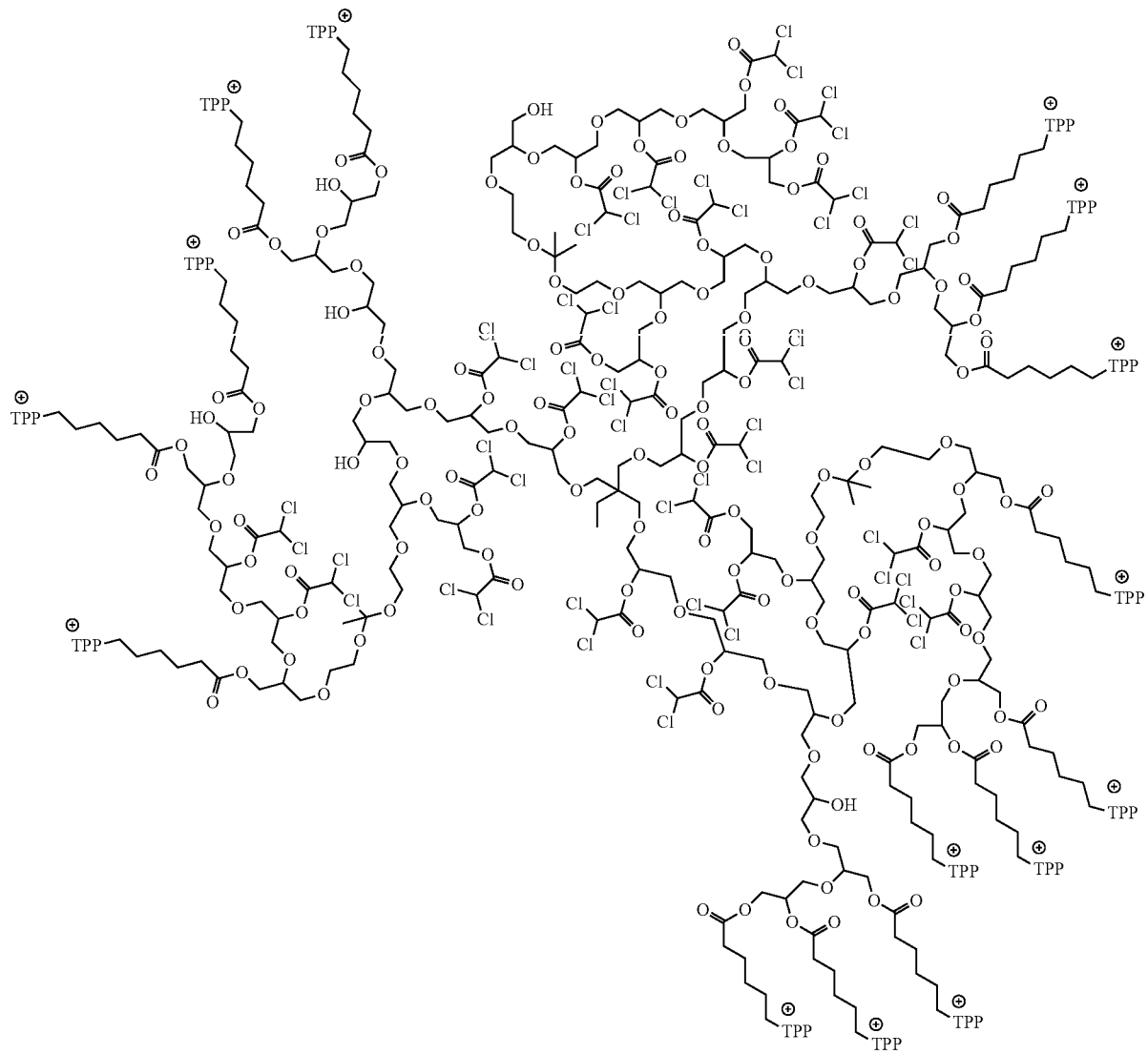

In specific examples, disclosed are compound comprising from 4 to 64 triphenyl phosphenyl moieties and from 4 to 64 dichloroacetyl moieties.

Nanoparticles

In certain aspects, the disclosed compounds can be incorporated into nanoparticles. Suitable nanoparticles include a core and one or more of the compounds disclosed herein. The disclosed compounds can be contained or embedded within the core. The disclosed compounds are preferably released from the core at a desired rate. The core is biodegradable and releases the disclosed compounds as the core is degraded or eroded. The targeting moieties preferably extend outwardly from the core so that they are available for outer surface. The core can also or alternatively include block copolymers that have hydrophobic portions and hydrophilic portions that can self-assemble in an aqueous environment into particles having the hydrophobic core and a hydrophilic out surface. In certain examples, the core comprises one or more biodegradable polymer or a polymer having a biodegradable portion.

Any suitable synthetic or natural biodegradable polymers can be used. Such polymers are recognizable and identifiable by one or ordinary skill in the art. Non-limiting examples of synthetic, biodegradable polymers include: poly(amides) such as poly(amino acids) and poly(peptides); poly(esters) such as poly(lactic acid), poly(glycolic acid), poly(lactic-co-glycolic acid) (PLGA), and poly(caprolactone); poly(anhydrides); poly(orthoesters); poly(carbonates); and chemical derivatives thereof (substitutions, additions of chemical groups, for example, alkyl, alkylene, hydroxylations, oxidations, and other modifications routinely made by those skilled in the art), fibrin, fibrinogen, cellulose, starch, collagen, and hyaluronic acid, copolymers and mixtures thereof. The properties and release profiles of these and other suitable polymers are known or readily identifiable.

In various examples, described herein the core comprises PLGA. PLGA is a well-known and well-studied hydrophobic biodegradable polymer used for the delivery and release of therapeutic agents at desired rates.

Preferably, at least some of the polymers used to form the core are amphiphilic having hydrophobic portions and hydrophilic portions. The hydrophobic portions can form the core, while the hydrophilic regions can for a shell that helps the nanoparticle evade recognition by the immune system and enhances circulation half-life. Examples of amphiphilic polymers include block copolymers having a hydrophobic block and a hydrophilic block. In various examples, the core is formed from hydrophobic portions of a block copolymer, a hydrophobic polymer, or combinations thereof.

Any suitable hydrophilic polymer can form a hydrophilic block of a block copolymer. Examples of suitable hydrophilic polymers include polysaccharides, dextran, chitosan, hyaluronic acid, and the like. In embodiments, polyethylene glycol (PEG) is a hydrophilic polymer used to serve as the hydrophilic portion of a block copolymer.

Nanoparticles, as described herein, can be of any suitable size. Generally, the nanoparticles are of a diametric dimension of less than about 999 nanometers, such as less than about 750 nm, less than about 600 nm, less than about 500 nm, less than about 400 nm, less than about 300 nm, or less than about 200 nm. In addition, or alternatively, the nanoparticles can be of a diametric dimension of greater than about 5 nm. In embodiments, the nanoparticles are from about 30 nm to about 300 nm in diameter. In embodiments, the nanoparticles are separated according to size, such as from about 20 nm to about 40 nm, from about 40 nm to about 60 nm, from about 60 nm to about 80 nm, from about 80 nm to about 100 nm, or from about 100 nm to about 150 nm.

Nanoparticles, as described herein, can be synthesized or assembled via any suitable process. Preferably, the nanoparticles are assembled in a single step to minimize process variation. A single step process can include nanoprecipitation and self-assembly. The nanoparticles can be synthesized or assembled by dissolving or suspending hydrophobic components in an organic solvent, preferably a solvent that is miscible in an aqueous solvent used for precipitation. In certain examples, acetonitrile is used as the organic solvent, but any suitable solvent can be used. Hydrophilic components are dissolved in a suitable aqueous solvent, such as water, 4 wt % ethanol, or the like. The organic phase solution can be added drop wise to the aqueous phase solution to nanoprecipitate the hydrophobic components and allow self-assembly of the nanoparticle in the aqueous solvent.

A process for determining appropriate conditions for forming the nanoparticles can be as follows. Briefly, functionalized polymers and phospholipids may be co-dissolved in organic solvent mixtures (in embodiments, the phospholipids or functionalized phospholipids are dissolved in the aqueous solvent). This solution can be added drop wise into hot (e.g., 65° C.) aqueous solvent (e.g., water, 4 wt-% ethanol, etc.), whereupon the solvents will evaporate, producing nanoparticles with a hydrophobic core coated with phospholipids. The phospholipids used at this stage may be a mixture of non-functionalized phospholipids and functionalized phospholipids (e.g., conjugated to targeting moieties) that can also include a hydrophilic polymer component, such as PEG. Once a set of conditions where a high (e.g., >75%) level of compound loading has been achieved, contrast agents or additional therapeutic agents can be included in the nanoprecipitation and self-assembly of the nanoparticles.

The size of the nanoparticle produced can be varied by altering the ratio of hydrophobic core components to amphiphilic shell components. The choice of PEGylated lipids and bilayer forming phospholipids can affect resulting nanoparticle size. PEGylated lipids are known to form small micellar structures because of surface tension imposed by the PEG chains. NP size can also be controlled by changing the polymer length, by changing the mixing time, and by adjusting the ratio of organic to the phase. Prior experience with NPs from PLGA-b-PEG of different lengths suggests that NP size will increase from a minimum of about 20 nm for short polymers (e.g., PLGA3000-PEG750) to a maximum of about 150 nm for long polymers (e.g., PLGA1000,000-PEG10,000). Thus, molecular weight of the polymer will serve to adjust the size.

NP surface charge can be controlled by mixing polymers with appropriately charged end groups. Additionally, the composition and surface chemistry can be controlled by mixing polymers with different hydrophilic polymer lengths, branched hydrophilic polymers, or by adding hydrophobic polymers.

Once formed, the nanoparticles can be collected and washed via centrifugation, centrifugal ultrafiltration, or the like. If aggregation occurs, NPs can be purified by dialysis, can be purified by longer centrifugation at slower speeds, can be purified with the use surfactant, or the like.

Once collected, any remaining solvent can be removed and the particles can be dried, which should aid in minimizing any premature breakdown or release of components. The NPs can be freeze dried with the use of bulking agents such as mannitol, or otherwise prepared for storage prior to use.

Pharmaceutical Compositions

The compounds described herein can be provided in a pharmaceutical composition. Depending on the intended mode of administration, the pharmaceutical composition can be in the form of solid, semi-solid or liquid dosage forms, such as, for example, tablets, suppositories, pills, capsules, powders, liquids, or suspensions, preferably in unit dosage form suitable for single administration of a precise dosage. The compositions will include a therapeutically effective amount of the compound described herein or derivatives thereof in combination with a pharmaceutically acceptable carrier and, in addition, can include other medicinal agents, pharmaceutical agents, carriers, or diluents. By pharmaceutically acceptable is meant a material that is not biologically or otherwise undesirable, which can be administered to an individual along with the selected compound without causing unacceptable biological effects or interacting in a deleterious manner with the other components of the pharmaceutical composition in which it is contained.

As used herein, the term carrier encompasses any excipient, diluent, filler, salt, buffer, stabilizer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in, e.g., *Remington's Pharmaceutical Sciences,* 21st Edition, ed. University of the Sciences in Philadelphia, Lippincott, Williams & Wilkins, Philadelphia Pa., 2005. Examples of physiologically acceptable carriers include saline, glycerol, DMSO, buffers such as phosphate buffers, citrate buffer, and buffers with other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™ (ICI, Inc.; Bridgewater, N.J.), polyethylene glycol (PEG), and PLURONICS™ (BASF; Florham Park, N.J.). To provide for the administration of such dosages for the desired therapeutic treatment, compositions disclosed herein can advantageously comprise between about 0.1% and 99%, and especially, 1 and 15% by weight of the total of one or more of the subject compounds based on the weight of the total composition including carrier or diluent.

Compositions containing the compound described herein or derivatives thereof suitable for parenteral injection can comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions can also contain adjuvants such as preserving, wetting, emulsifying, and dispensing agents. Prevention of the action of microorganisms can be promoted by various antibacterial and antifungal agents, for example, parabens, chlorobutanol, phenol, sorbic acid, and the like. Isotonic agents, for example, sugars, sodium chloride, and the like can also be included. Prolonged absorption of the injectable pharmaceutical form can be brought about by the use of agents delaying absorption, for example, aluminum monostearate and gelatin.

Solid dosage forms for oral administration of the compounds described herein or derivatives thereof include capsules, tablets, pills, powders, and granules. In such solid dosage forms, the compounds described herein or derivatives thereof is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms can also comprise buffering agents.

Solid compositions of a similar type can also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others known in the art. They can contain opacifying agents and can also be of such composition that they release the active compound or compounds in a certain part of the intestinal tract in a delayed manner. Examples of embedding compositions that can be used are polymeric substances and waxes. The active compounds can also be in micro-encapsulated form, if appropriate, with one or more of the above-mentioned excipients. The disclosed compounds can also be incorporated into polymers, examples of which include poly (D-L lactide-co-glycolide) polymer for intracranial tumors; poly[bis(pcarboxyphenoxy) propane:sebacic acid] in a 20:80 molar ratio (as used in GLIADEL); chondroitin; chitin; and chitosan.

Liquid dosage forms for oral administration of the compounds described herein or derivatives thereof include pharmaceutically acceptable emulsions, solutions, suspensions, syrups, and elixirs. In addition to the active compounds, the liquid dosage forms can contain inert diluents commonly used in the art, such as water or other solvents, solubilizing agents, and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil, sesame oil, glycerol, tetrahydrofurfuryl alcohol, polyethyleneglycols, and fatty acid esters of sorbitan, or mixtures of these substances, and the like.

Besides such inert diluents, the composition can also include additional agents, such as wetting, emulsifying, suspending, sweetening, flavoring, or perfuming agents.

Suspensions, in addition to the active compounds, can contain additional agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these s stances, and the like.

Compositions of the compounds described herein or derivatives thereof for rectal administrations are optionally suppositories, which can be prepared by mixing the compounds with suitable non-irritating excipients or carriers such as cocoa butter, polyethyleneglycol or a suppository wax, which are solid at ordinary temperatures but liquid at body temperature and therefore, melt in the rectum or vaginal cavity and release the active component.

Dosage forms for topical administration of the compounds described herein or derivatives thereof include ointments, powders, sprays, and inhalants. The compounds described herein or derivatives thereof are admixed under sterile conditions with a physiologically acceptable carrier and any preservatives, buffers, or propellants as can be required. Ophthalmic formulations, ointments, powders, and solutions are also contemplated as being within the scope of the compositions.

The compositions can include one or more of the compounds described herein and a pharmaceutically acceptable carrier. As used herein, the term pharmaceutically acceptable salt refers to those salts of the compound described herein or derivatives thereof that are, within the scope of sound medical judgment, suitable for use in contact with the tissues of subjects without undue toxicity, irritation, allergic response, and the like, commensurate with a reasonable benefit/risk ratio, and effective for their intended use, as well as the zwitterionic forms, where possible, of the compounds described herein. The term salts refers to the relatively non-toxic, inorganic and organic acid addition salts of the compounds described herein. These salts can be prepared in situ during the isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate, methane sulphonate, and laurylsulphonate salts, and the like. These can include cations based on the alkali and alkaline earth metals, such as sodium, lithium, potassium, calcium, magnesium, and the like, as well as non-toxic ammonium, quaternary ammonium, and amine cations including, but not limited to ammonium, tetramethylammonium, tetraethylammonium, methylamine, dimethylamine, trimethylamine, triethylamine, ethylamine, and the like. (See S. M. Barge et al., *J. Pharm. Sci.* (1977) 66, 1, which is incorporated herein by reference in its entirety, at least, for compositions taught herein.)

Administration of the compounds and compositions described herein or pharmaceutically acceptable salts thereof to a subject can be carried out using therapeutically effective amounts of the compounds and compositions described herein or pharmaceutically acceptable salts thereof as described herein for periods of time effective to treat a disorder.

The effective amount of the compounds and compositions described herein or pharmaceutically acceptable salts thereof as described herein can be determined by one of ordinary skill in the art and includes exemplary dosage amounts for a mammal of from about 0.5 to about 200 mg/kg of body weight of active compound per day, which can be administered in a single dose or in the form of individual divided doses, such as from 1 to 4 times per day. Alternatively, the dosage amount can be from about 0.5 to about 150 mg/kg of body weight of active compound per day, about 0.5 to 100 mg/kg of body weight of active compound per day, about 0.5 to about 75 mg/kg of body weight of active compound per day, about 0.5 to about 50 mg/kg of body weight of active compound per day, about 0.5 to about 25 mg/kg of body weight of active compound per day, about 1 to about 20 mg/kg of body weight of active compound per day, about 1 to about 10 mg/kg of body weight of active compound per day, about 20 mg/kg of body weight of active compound per day, about 10 mg/kg of body weight of active compound per day, or about 5 mg/kg of body weight of active compound per day. The expression effective amount, when used to describe an amount of compound in a method, refers to the amount of a compound that achieves the desired pharmacological effect or other effect, for example an amount that results in enzyme inhibition.

Those of skill in the art will understand that the specific dose level and frequency of dosage for any particular subject can be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition.

Activity Assays

The activity of the compounds provided herein as anti-cancer agents can be measured in standard assays, e.g., HPLC assays. The activities of the compounds as determined using the assays described herein can be reported in terms of $IC_{50}$. As used herein, $IC_{50}$ refers to an amount, concentration, or dosage of a particular test compound that achieves a 50% inhibition of a maximal response in an assay that measures such response.

In certain aspects, the disclosed compounds and compositions need not actually be synthesized, but instead can be used as targets for any molecular modeling technique to predict and characterize interactions with cancer associated enzymes. This is achieved through structural information and computer modeling. Computer modeling technology allows visualization of the three-dimensional atomic structure of a selected molecule and the rational design of new compounds that will interact with an enzyme. The three-dimensional construct of the enzyme typically depends on data from x-ray crystallographic analyses or NMR imaging of the selected molecule. The molecular dynamics require force field data (e.g., Merck Molecular Force Field). The computer graphics systems enable prediction of how a new compound will link to the enzyme and allow experimental manipulation of the structures of the compound to perfect binding specificity. Prediction of what the interactions will be when small changes are made in one or both requires molecular mechanics software and computationally intensive computers, usually coupled with user-friendly, menu-driven interfaces between the molecular design program and the user.

Examples of molecular modeling systems are the CHARMm and QUANTA programs, Polygen Corporation, Waltham, Mass. CHARMm performs the energy minimization and molecular dynamics functions. QUANTA performs the construction, graphic modeling and analysis of molecular structure. QUANTA allows interactive construction, modification, visualization, and analysis of the behavior of molecules with each other. Upon identification of compounds that interact in a desired way with the enzyme in silico, actual compounds can be synthesized and assayed as disclosed herein.

Methods of Use

Provided herein are methods of treating, preventing, or ameliorating cancer in a subject. The methods include administering to a subject an effective amount of one or more of the compounds or compositions described herein, or a pharmaceutically acceptable salt thereof. The compounds and compositions described herein or pharmaceutically acceptable salts thereof are useful for treating cancer in humans, e.g., pediatric and geriatric populations, and in animals, e.g., veterinary applications. The disclosed methods can optionally include identifying a patient who is or can be in need of treatment of a cancer. Examples of cancer types treatable by the compounds and compositions described herein include bladder cancer, brain cancer, breast cancer, colorectal cancer, cervical cancer, gastrointestinal cancer, genitourinary cancer, head and neck cancer, lung cancer, ovarian cancer, pancreatic cancer, prostate cancer, renal cancer, skin cancer, and testicular cancer. Further examples include cancer and/or tumors of the anus, bile duct, bone, bone marrow, bowel (including colon and rectum), eye, gall bladder, kidney, mouth, larynx, esophagus, stomach, testis, cervix, mesothelioma, neuroendocrine, penis, skin, spinal cord, thyroid, vagina, vulva, uterus, liver, muscle, blood cells (including lymphocytes and other immune system cells). Specific cancers contemplated for treatment include carcinomas, Karposi's sarcoma, melanoma, mesothelioma, soft tissue sarcoma, pancreatic cancer, lung cancer, leukemia (acute lymphoblastic, acute myeloid, chronic lymphocytic, chronic myeloid, and other), and lymphoma (Hodgkin's and non-Hodgkin's), and multiple myeloma. Treatment of breast cancer by administering the disclosed compounds is particularly preferred.

Cancers that are preferably treated by the disclosed methods using the compounds disclosed herein are lung, breast, brain, ovarian, lymphoma, leukemia, head and neck, pancreatic, and cervical, colon and rectum, endrometrial, esophagous, liver, penile, skin-melanoma, skin-nonmelanoma, stomach, testicular, vaginal, uterine, vulvar, paranasal cancer, uropharyngeal and laryngeal cancers.

The methods of treatment or prevention described herein can further include treatment with one or more additional agents (e.g., an anti-cancer agent or ionizing radiation). The one or more additional agents and the compounds and compositions or pharmaceutically acceptable salts thereof as described herein can be administered in any order, including simultaneous administration, as well as temporally spaced order of up to several days apart. The methods can also include more than a single administration of the one or more additional agents and/or the compounds and compositions or pharmaceutically acceptable salts thereof as described herein. The administration of the one or more additional agents and the compounds and compositions or pharmaceutically acceptable salts thereof as described herein can be by the same or different routes. When treating with one or more additional agents, the compounds and compositions or pharmaceutically acceptable salts thereof as described herein can be combined into a pharmaceutical composition that includes the one or more additional agents.

For example, the compounds or compositions or pharmaceutically acceptable salts thereof as described herein can be combined into a pharmaceutical composition with an additional anti-cancer agent, such as 13-cis-Retinoic Acid, 2-Amino-6-Mercaptopurine, 2-CdA, 2-Chlorodeoxyadenosine, 5-fluorouracil, 6-Thioguanine, 6-Mercaptopurine, Accutane, Actinomycin-D, Adriamycin, Adrucil, Agrylin, Ala-Cort, Aldesleukin, Alemtuzumab, Alitretinoin, Alkaban-AQ, Alkeran, All-transretinoic acid, Alpha interferon, Altretamine, Amethopterin, Amifostine, Aminoglutethimide, Anagrelide, Anandron, Anastrozole, Arabininosylcytosine, Aranesp, Aredia, Arimidex, Aromasin, Arsenic trioxide, Asparaginase, ATRA, Avastin, BCG, BCNU, Bevacizumab, Bexarotene, Bicalutamide, BiCNU, Blenoxane, Bleomycin, Bortezomib, Busulfan, Busulfex, C225, Calcium Leucovorin, Campath, Camptosar, Camptothecin-11, Capecitabine, Carac, Carboplatin, Carmustine, Carmustine wafer, Casodex, CCNU, CDDP, CeeNU, Cerubidine, cetuximab, Chlorambucil, Cisplatin, Citrovorum Factor, Cladribine, Cortisone, Cosmegen, CPT-11, Cyclophosphamide, Cytadren, Cytarabine, Cytarabine liposomal, Cytosar-U, Cytoxan, Dacarbazine, Dactinomycin, Darbepoetin alfa, Daunomycin, Daunorubicin, Daunorubicin hydrochloride, Daunorubicin liposomal, DaunoXome, Decadron, Delta-Cortef, Deltasone, Denileukin diftitox, DepoCyt, Dexamethasone, Dexamethasone acetate, Dexamethasone sodium phosphate, Dexasone, Dexrazoxane, DHAD, DIC, Diodex, Docetaxel, Doxil, Doxorubicin, Doxorubicin liposomal, Droxia, DTIC, DTIC-Dome, Duralone, Efudex, Eligard, Ellence, Eloxatin, Elspar, Emcyt, Epirubicin, Epoetin alfa, Erbitux, Erwinia L-asparaginase, Estramustine, Ethyol, Etopophos, Etoposide, Etoposide phosphate, Eulexin, Evista, Exemestane, Fareston, Faslodex, Femara, Filgrastim, Floxuridine, Fludara, Fludarabine, Fluoroplex, Fluorouracil, Fluorouracil (cream), Fluoxymesterone, Flutamide, Folinic Acid, FUDR, Fulvestrant, G-CSF, Gefitinib, Gemcitabine, Gemtuzumab ozogamicin, Gemzar, Gleevec, Lupron, Lupron Depot, Matulane, Maxidex, Mechlorethamine, Mechlorethamine Hydrochlorine, Medralone, Medrol, Megace, Megestrol, Megestrol Acetate, Melphalan, Mercaptopurine, Mesna, Mesnex, Methotrexate, Methotrexate Sodium, Methylprednisolone, Mylocel, Letrozole, Neosar, Neulasta, Neumega, Neupogen, Nilandron, Nilutamide, Nitrogen Mustard, Novaldex, Novantrone, Octreotide, Octreotide acetate, Oncospar, Oncovin, Ontak, Onxal, Oprevelkin, Orapred, Orasone, Oxaliplatin, Paclitaxcl, Pamidronate, Panretin, Paraplatin, Pediapred, PEG Interferon, Pegaspargase, Pegfilgrastim, PEG-INTRON, PEG-L-asparaginase, Phenylalanine Mustard, Platinol, Platinol-AQ, Prednisolone, Prednisone, Prelone, Procarbazine, PROCRIT, Proleukin, Prolifeprospan 20 with Carmustine implant, Purinethol, Raloxifene, Rheumatrex, Rituxan, Rituximab, Roveron-A (interferon alfa-2a), Rubex, Rubidomycin hydrochloride, Sandostatin, Sandostatin LAR, Sargramostim, Solu-Cortef, Solu-Medrol, STI-571, Streptozocin, Tamoxifen, Targretin, Taxol, Taxotere, Temodar, Temozolomide, Teniposide, TESPA, Thalidomide, Thalomid, TheraCys, Thioguanine, Thioguanine Tabloid, Thiophosphoamide, Thioplex, Thiotepa, TICE, Toposar, Topotecan, Toremifene, Trastuzumab, Tretinoin, Trexall, Trisenox, TSPA, VCR, Velban, Velcade, VePesid, Vesanoid, Viadur, Vinblastine, Vinblastine Sulfate, Vincasar Pfs, Vincristine, Vinorelbine, Vinorelbine tartrate, VLB, VP-16, Vumon, Xeloda, Zanosar, Zevalin, Zinecard, Zoladex, Zoledronic acid, Zometa, Gliadel wafer, Glivec, GM-CSF, Goserelin, granulocyte colony stimulating factor, Halotestin, Herceptin, Hexadrol, Hexalen, Hexamethylmelamine, HMM, Hycamtin, Hydrea, Hydrocort Acetate, Hydrocortisone, Hydrocortisone sodium phosphate, Hydrocortisone sodium succinate, Hydrocortone phosphate, Hydroxyurea, Ibritumomab, Ibritumomab Tiuxetan, Idamycin, Idarubicin, Ifex, IFN-alpha, Ifosfamide, IL 2, IL-11, Imatinib mesylate, Imidazole Carboxamide, Interferon alfa, Interferon Alfa-2b (PEG conjugate), Interleukin 2, Interleukin-11, Intron A (interferon alfa-2b), Leucovorin, Leukeran, Leukine, Leuprolide, Leurocristine, Leustatin, Liposomal Ara-C, Liquid Pred, Lomustine, L-PAM, L-Sarcolysin, Meticorten, Mitomycin, Mitomycin-C, Mitoxantrone, M-Prednisol, MTC, MTX, Mustargen, Mustine, Mutamycin, Myleran, Iressa, Irinotecan, Isotretinoin, Kidrolase, Lanacort, L-asparaginase, and LCR. The additional anti-cancer agent can also include biopharmaceuticals such as, for example, antibodies.

Many tumors and cancers have viral genome present in the tumor or cancer cells. For example, Epstein-Barr Virus (EBV) is associated with a number of mammalian malignancies. The compounds disclosed herein can also be used alone or in combination with anticancer or antiviral agents, such as ganciclovir, azidothymidine (AZT), lamivudine (3TC), etc., to treat patients infected with a virus that can cause cellular transformation and/or to treat patients having a tumor or cancer that is associated with the presence of viral genome in the cells. The compounds disclosed herein can also be used in combination with viral based treatments of oncologic disease. For example, the compounds can be used with mutant herpes simplex virus in the treatment of non-small cell lung cancer (Toyoizumi, et al., "Combined therapy with chemotherapeutic agents and herpes simplex virus type IICP34.5 mutant (HSV-1716) in human non-small cell lung cancer," *Human Gene Therapy,* 1999, 10(18):17).

DCA delivery to the mitochondria resulted in significant reduction in lactate levels and played important roles in modulating dendritic cell (DC) phenotype evidenced by secretion of interleukin-12 from DCs upon activation with tumor antigens from MITO-DCA treated cancer cells. Targeting mitochondrial metabolic inhibitors (e.g., IM) to the mitochondria could lead to the induction of an efficient anti-tumor immune response thus introducing the concept of combining glycolysis inhibition with immune system to destroy tumor. As such, the disclosed compounds can be combined (in the same composition, co-administered, or administered as part of a treatment regimen) with anti-cancer immunotherapies such as CPG-ODN. In further examples, the disclosed compounds can be combined with (in the same composition, co-administered, or administered as part of a treatment regimen) Sipuleucel-T (Provenge), Alemtuzumab, Bevacizumab, Brentuximab vedotin, Cetuximab, Gemtuzumab ozogamicin, Ibritumomab tiuxetan, Ipilimumab, Ofatumumab, Panitumumab, Rituximab, Tositumomab, or Trastuzumab. In further examples, the disclosed compounds can be combined with (in the same composition, co-administered, or administered as part of a treatment regimen) interleukin-2 and interferon-α.

Also described herein are methods of killing a tumor cell in a subject. The method includes contacting the tumor cell with an effective amount of a compound or composition as described herein, and optionally includes the step of irradiating the tumor cell with an effective amount of ionizing radiation. Additionally, methods of radiotherapy of tumors are provided herein. The methods include contacting the tumor cell with an effective amount of a compound or composition as described herein, and irradiating the tumor with an effective amount of ionizing radiation. As used herein, the term ionizing radiation refers to radiation comprising particles or photons that have sufficient energy or can produce sufficient energy via nuclear interactions to produce ionization. An example of ionizing radiation is x-radiation. An effective amount of ionizing radiation refers to a dose of ionizing radiation that produces an increase in cell damage or death when administered in combination with the compounds described herein. The ionizing radiation can be delivered according to methods as known in the art, including administering radiolabeled antibodies and radioisotopes.

The methods and compounds as described herein are useful for both prophylactic and therapeutic treatment. As used herein the term treating or treatment includes prevention; delay in onset; diminution, eradication, or delay in exacerbation of signs or symptoms after onset; and prevention of relapse. For prophylactic use, a therapeutically effective amount of the compounds and compositions or pharmaceutically acceptable salts thereof as described herein are administered to a subject prior to onset (e.g., before obvious signs of cancer), during early onset (e.g., upon initial signs and symptoms of cancer), or after an established development of cancer. Prophylactic administration can occur for several days to years prior to the manifestation of symptoms of an infection. Prophylactic administration can be used, for example, in the chemopreventative treatment of subjects presenting precancerous lesions, those diagnosed with early stage malignancies, and for subgroups with susceptibilities (e.g., family, racial, and/or occupational) to particular cancers. Therapeutic treatment involves administering to a subject a therapeutically effective amount of the compounds and compositions or pharmaceutically acceptable salts thereof as described herein after cancer is diagnosed.

Kits

Also provided herein are kits for treating or preventing cancer in a subject. A kit can include any of the compounds or compositions described herein. For example, a kit can include a compound of Formula I. A kit can further include one or more anti-cancer agents (e.g., paclitaxel). A kit can include an oral formulation of any of the compounds or compositions described herein. A kit can additionally include directions for use of the kit (e.g., instructions for treating a subject).

The examples below are intended to further illustrate certain aspects of the methods and compounds described herein, and are not intended to limit the scope of the claims.

EXAMPLES

The following examples are set forth below to illustrate the methods and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, temperatures, pressures, and other reaction ranges and conditions that can be used to optimize the product purity and yield obtained from the described process.

All chemicals were received and used without further purification unless otherwise noted. Dichloroacetetic (DCA) anhydride, tris(hydroxymethyl)aminomethane (Tris), triphenylphosphine (TPP), 6-bromohexanoic acid, N-ethoxycarbonyl-2-ethoxy-1,2-dihydroquinoline (EEDQ), 3-bromopropanol, 4-dimethylaminopyridine (DMAP), (3-(4,5-dimethylthiazol-2-yl)-2,5-diphenyltetrazolium bromide (MTT), and adenosine 5'-triphosphate (ATP) disodium salt hydrate were purchased from Sigma-Aldrich. JC-1 was procured from Invitrogen. ALEXA FLUOR™ 488 Annexin V/Dead cell apoptosis kit was purchased from Invitrogen. Lactate assay kit was obtained from BioVision, CA, USA. CELLTITER-GLO™ luminescent cell viability assay kit from Promega was used to quantify cellular ATP content. Granulocyte-macrophage colony-stimulating factor (GM-CSF) was purchased from R&D systems. Interleukin (IL)-6, IL-2, IL-10, interferon-gamma (IFN-γ), IL-12, IL-4, and tumour necrosis factor (TNF)-α cytokines were tested using BD OptEIA mouse enzyme-linked immnunosorbent assay (ELISA) kits. Ultra pure lipopolysaccharide (LPS) was purchased from Invivogen, CA, USA. CD11c microbeads for dendritic cell (DC) purification was purchased from Miltenyl Biotech, CA USA. Electrospray ionization mass spectrometry (ESI-MS) and high-resolution mass spectrometry (HRMS)-ESI were recorded on Perkin Elmer SCIEX API 1 plus and Thermo scientific ORBITRAP ELITE instruments, respectively.

Distilled water was purified by passage through a Millipore Milli-Q Biocel water purification system (18.2 MΩ) containing a 0.22 μm filter. $^1$H and $^{13}$C NMR spectra were recorded on a 400 MHz Varian NMR spectrometer and $^{31}$P NMR spectra were recorded on a 500 MHz Varian NMR spectrometer. High-performance liquid chromatography (HPLC) analyses were made on an Agilent 1200 series instrument equipped with a multi-wavelength UV-visible and a fluorescence detector. Flow cytometry studies were performed on a BD LSRII flow cytometer equipped with digital acquisition using FACSDiva v6. Plate reader analysis was performed on a Bio-Tek Synergy HT microplate reader. Confocal images were recorded in a Nikon A1 confocal microscope. X-ray intensity data were collected at 100 K on a Bruker APEX CCD diffractometer.

Human prostate cancer LNCaP, PC3, and DU145 were procured from the American type culture collection (ATCC). Human bone marrow derived MSC cells were also purchased from Lonza. DU145 cells were grown at 37° C. in 5% $CO_2$ in Eagle's minimum essential medium (EMEM) supplemented with 10% fetal bovine serum (FBS) and 1% penicillin/streptomycin. LNCaP and PC3 cells were grown in Roswell Park Memorial Institute (RPMI) 1640 medium. MSC cells were grown in MSC basal medium supplemented with MSC growth kit-low serum components and 2% FBS. Cells were passed every 3 to 4 days and restarted from frozen stocks upon reaching pass number 20 for PC3, LNCaP, DU145, and 10 for MSC.

Animals were obtained from Jackson Laboratory and handled in accordance with "The guide for the Care and Use of Laboratory Animals" of American Association for Accreditation of Laboratory Animal Care (AAALAC), Animal Welfare Act (AWA), and other applicable federal and state guidelines. All animal work presented here was approved by Institutional Animal Care and Use Committee (IACUC) of University of Georgia.

Example 1: Synthesis of TPP-(CH$_2$)$_5$—COOH

A mixture of 6-bromohexanoic acid (2.0 g, 10.3 mmol) and TPP (2.8 g, 10.8 mmol) was heated to reflux for 24 h in acetonitrile. The solvent was evaporated to dryness. The resulting residue was washed with hexane-diethyl ether (3×30 mL) followed by vacuum drying to afford a white solid as a pure product. Yield: 91% (4 g). Melting point: 200-205° C.; $^1$H NMR (CDCl$_3$): δ 9.3 (s, 1H), 7.6-7.8 (m, 15H), 3.5 (t, 2H), 2.3 (t, 2H), 1.6 (m, 6H). $^{13}$C NMR (CDCl$_3$): δ 175, 135, 133.6, 130.6, 118.5, 34.2, 29.37, 23.9, 22.8, 22.29, 21.9. $^{31}$P NMR (CDCl$_3$) 24.34. ppm. HRMS-ESI (m/z): [M-Br]$^+$ calcd. for $C_{24}H_{26}O_2P^+$, 377.1665. found, 377.1629.

Example 2: Synthesis of TPP-Tris-(OH)$_3$

TPP-(CH$_2$)$_5$—COOH (0.50 g, 1.1 mmol), Tris (0.15 g, 1.2 mmol), and EEDQ (0.32 g, 1.3 mmol) were dissolved in ethanol. This mixture was stirred at 50° C. for 12 h followed by drying under vacuum. The crude mixture was recrystallized 3-4 times using ethanol/CH$_2$Cl$_2$/diethyl ether to give a white solid of TPP-Tris-(OH)$_3$ in 86% yield (0.52 g). Melting point: 115-120° C.; $^1$H NMR (CDCl$_3$): 7.7 (m, 15H), 3.7 (s, 6H), 3.5 (t, 2H), 2.4 (t, 2H), 1.7 (m, 6H) ppm. $^{13}$C NMR (CDCl$_3$): δ 175.6, 135.2, 133.6, 130.6, 118.4, 113.2, 64.1, 62.3, 36.2, 29.3, 24.9, 22.5, 21.5. $^{31}$P NMR (CDCl$_3$) 24.28 ppm. HRMS-ESI (m/z): [M-Br]$^+$ calcd. for $C_{28}H_{35}NO_4P^+$, 480.2298. found, 480.2243.

Example 3: Synthesis of MITO-DCA

A solution of TPP-Tris-(OH)$_3$ (0.5 g, 0.9 mmol) in anhydrous CH$_2$Cl$_2$ (10 mL) was prepared in a round bottom flask equipped with nitrogen flow. DCA anhydride (2.13 g, 8.9 mmol) was added drop wise to the solution. The reaction was stirred overnight at room temperature and the progress of the reaction was monitored by thin layer chromatography using a mixture of CH$_2$Cl$_2$ and CH$_3$OH. The solvent was evaporated to dryness and MITO-DCA was purified by using silica gel chromatography (CH$_2$Cl$_2$:CH$_3$OH, 95:5). Yield, 35% (0.3 g). Melting point: 80-85° C.; $^1$H NMR (CDCl$_3$): 8.3 (broad s, 1H), 7.8-7.7 (m, 15H), 6.22 (s, 3H), 4.72 (s, 6H), 3.50 (t, 2H), 2.38 (t, 2H), 1.69 (m, 6H) ppm. $^{13}$C NMR (CDCl$_3$): δ 175.2, 163.8, 135.2, 133.6, 130.6, 118.5, 64.6, 64.5, 57.9, 36.3, 29.5, 24.4, 22.8, 20.9 ppm. $^{31}$P NMR (CDCl$_3$) 24.59 ppm. HRMS-ESI (m/z): [M-Br]$^+$ calcd. for $C_{34}H_{35}C_6NO_7P^+$, 810.0277. found, 810.0258. Single crystals suitable for X-ray analysis were grown in CH$_2$Cl$_2$ and diethyl ether mixture.

Example 4: Synthesis of TPP-(CH$_2$)$_3$—OH

A mixture of 3-bromopropanol (1.0 g, 7.2 mmol) and TPP (2.1 g, 7.9 mmol) in toluene (25 mL) was heated to reflux for 24 h. The resulting white precipitate was filtered through fritted glass followed by the washing with diethyl ether (3×30 mL). The white solid was dried under vacuum to get the pure product of TPP-(CH$_2$)$_3$—OH. Yield, 61% (1.7 g). Melting point: 235-240° C.; $^1$H NMR (CDCl$_3$): 7.65-7.80 (m, 15H), 4.94 (t, 1H), 3.70-3.83 (m, 4H), 1.81 (m, 2H) ppm. $^{13}$C NMR (CDCl$_3$): δ 135.09, 133.47, 130.51, 118.72, 60.40, 25.92, 20.43 ppm. $^{31}$P NMR (CDCl$_3$) 24.77 ppm. HRMS-ESI (m/z): [M-Br]$^+$ calcd. for $C_{21}H_{22}OP^+$, 321.1403. found, 321.1403.

Example 5: Synthesis of TPP-DCA

A solution of TPP-(CH$_2$)$_3$—OH (0.25 g, 0.623 mmol) in anhydrous CH$_2$Cl$_2$ (15 mL) was prepared in a round bottom flask equipped with nitrogen flow. DCA anhydride (0.45 g, 1.86 mmol) was added drop wise to the solution. The reaction was stirred overnight at room temperature and monitored by TLC (CH$_2$Cl$_2$/CH$_3$OH, 90:10). The solvent was evaporated to dryness to get pasty mass, which was further purified by using silica gel chromatography (CH$_2$Cl$_2$/CH$_3$OH, 90:10). Yield, 48% (0.15 g). Melting point: 75-80° C.; $^1$H NMR (CDCl$_3$): 7.68-7.89 (m, 15H), 6.17 (s, 1H), 4.64 (broad t, 2H), 4.13 (broad t, 2H), 2.06 (broad, 2H) ppm. $^{13}$C NMR (CDCl$_3$): δ 164.27, 135.17, 133.76, 130.49, 118.27, 66.05, 64.54, 30.90, 22.16 ppm. $^{31}$P (CDCl$_3$) NMR: 25.01 ppm. HRMS-ESI (m/z): [M-Br]$^+$ calcd. for $C_{23}H_{22}Cl_2O_2P^+$, 431.0729. found, 431.0687.

Example 6: HPLC Studies

HPLC studies were carried out using an Agilent 1200 series instrument to explore the purity of the samples. A 5 µL of 5 mM solution of MITO-DCA in DMSO was injected using a Zoebax C18 column and a 50:50 acetonitrile: isopropanol-1% trifluoroacetic acid (TFA) as mobile phase. The wavelength used for these experiments was 268 nm. HPLC showed a single peak confirming purity of the compounds.

Example 7: Solubility and Stability Studies

Solubility of MITO-DCA in water was checked by preparing different concentration of MITO-DCA ranging from 2 µM to 5 mM in DMSO (0.1-2.5%)-phosphate buffered saline (PBS). At all concentrations, MITO-DCA was transparent. The solubility of MITO-DCA was far higher than that of DCA in an organic solvent showing its lipophilicity for mitochondrial uptake.

For stability study, a 5 mM solution of MITO-DCA or TPP-DCA in 10% DMSO in PBS was incubated for 36 h at room temperature. This solution was used in ESI-MS experiments to check the degradation behavior of TPP compounds.

Example 8: Single-Crystal X-Ray Diffraction

Colorless crystals of MITO-DCA suitable for X-ray diffraction were grown by slow diffusion of diethyl ether into a saturated solution of MITO-DCA in dichloromethane at 25° C. A single crystal was mounted on the top of a glass fiber. Intensity data were collected at 100 K on a Bruker APEX CCD diffractometer using the SMART software, with Mo-Kα radiation ($\lambda$=0.71073 Å) using w-scan technique. The data were collected in 1464 frames with 10 sec exposure. The SAINT software was used for data integration. The structure was solved by direct methods using the SHELXTL 6.1 software package. Non-hydrogen atomic scattering factors were taken from the literature tabulations. Non-hydrogen atoms were located from successive difference Fourier map calculations. Empirical absorption corrections were applied with SADABS. One O atom and two Cl atoms in the cation of molecule were found disordered in two sets, for the O atom labeled as O(5) (one set) and O(5') (another set), for the two Cl atoms labeled as Cl(3), Cl(4) (one set) and Cl(3'), Cl(4') (another set), respectively. Each of these two sets is divided using the PART commands with proper restraints and refined occupancies. The set of O(5) has 73.379% occupancies while the other (O(5')) has 26.621% occupancies. The set of Cl(3), Cl(4) has 81.997% occupancies while the other (Cl(3'), Cl(4')) has 18.003% occupancies. In the final cycles of each refinement, all the non-hydrogen atoms were refined in anisotropic displacement parameters. The hydrogen atom positions were calculated and allowed to ride on the carbon to which they are bonded assuming a C—H bond length of m A (m=1.00 for CH groups, m=0.99 for $CH_2$ groups, m=0.98 for $CH_3$ groups, m=0.95 for Ph-H groups). Hydrogen atom temperature factors were fixed at n (n=1.2 for CH and $CH_7$ groups groups, n=1.5 for $CH_3$ groups, n=1.2 for Ph-H groups) times the isotropic temperature factor of the C-atom to which they are bonded. A perspective view of MITO-DCA was obtained with ORTEP. Crystal structure data for MITO-DCA can be accessed from the Cambridge Crystallographic Data Centre with accession number CCDC 940383.

Example 9: JC1 Assay

PC3 cells were cultured on a live cell imaging glass bottom dish at a density of $1\times10^6$ cells/mL and allowed to grow overnight at 37° C. Cells were treated with 150 μM Na-DCA, 150 μM TPP-DCA, and 50 μM MITO-DCA for 6 h at 37° C. A solution of JC-1 reagent (10 μg/mL in RPMI) was added and incubation was carried out at 37° C. for 20 min. The cells were washed 3 times with PBS, and live cell imaging was performed in phenol red free RPMI media.

Example 10: MTT Assay

The cytotoxic behaviors of MITO-DCA, TPP-DCA, Na-DCA, and TPP-Tris-$(OH)_3$ were evaluated using the MTT assay against PC3, DU145, LNCaP, and MSC cells. Cells (2000 cells/well for PC3, DU145, and MSC cells; 5000 cells/well for LNCaP) were seeded on a 96-well plate in 100 μL of desired medium and incubated for 24 h. The cells were treated with different DCA compounds and TPP-Tris-$(OH)_3$ at varying concentrations and incubated for 72 h at 37° C. The cells were then treated with 20 μL of MTT (5 mg/mL in PBS) for 5 h. The medium was removed, the cells were lysed with 100 μL of DMSO, and the absorbance of the purple tormazan was recorded at 550 nm using a Bio-Tek Synergy HT microplate reader. Each well was performed in triplicate. All experiments were repeated three times. Cytotoxicity was expressed as mean percentage increase relative to the unexposed control±SD. Control values were set at 0% cytotoxicity or 100% cell viability. Cytotoxicity data (where appropriate) was fitted to a sigmoidal curve and a three parameters logistic model used to calculate the $IC_{50}$, which is the concentration of chemotherapeutics causing 50% inhibition in comparison to untreated controls. The mean $IC_{50}$ is the concentration of agent that reduces cell growth by 50% under the experimental conditions and is the average from at least three independent measurements that were reproducible and statistically significant. The $IC_{50}$ values were reported at ±99% confidence intervals. This analysis was performed with GraphPad Prism (San Diego, U.S.A).

Example 11: Apoptosis Detection

PC3 and MSC cells were seeded at a density of $1\times10^6$ cells/mL on each well of a six well plate and allowed to grow overnight. Cells were treated with 50 μM Na-DCA, 150 μM TPP-DCA, and 150 μM MITO-DCA for 12 h at 37° C. As positive controls, etoposide (100 μM, incubation time: 12 h) for apoptosis and $H_2O_2$ (1 mM, incubation time: 45 min) for necrosis were used. The cells were trypsinized, repeatedly washed, and centrifuged at 1,800 RPM for 3 min, and the supernatants were discarded. Cell density was determined and cells were resuspended in 1× annexin-binding buffer to ~$1\times10^6$ cells/mL preparing a sufficient volume to have 100 UL per assay. To 100 μL of cell suspension, 5 μL ALEXA FLUOR™ 488 annexin V and 1 UL 100 μg/mL PI working solution were added and incubated for 15 min at room temperature. After the incubation period, 400 μL 1× annexin-binding buffer was added to each sample, samples were gently mixed keeping the samples on ice and the samples were analyzed on the flow cytometer immediately.

Example 12: Cellular Lactate and ATP Determination

PC3, LNCaP, and MSC cells were seeded at a density of $1\times10^6$ cells/mL on each well of a 12 well plate and allowed to grow overnight at 37° C. under 5% $CO_2$. Cells were treated with 150 μM Na-DCA, 150 μM TPP-DCA, and 50 μM MITO-DCA for 6 h at 37° C. After 6 h, the media was removed and the cells were homogenized. The lysate was added to the enzyme and substrate working reagent mixture and incubated for 30 min. Lactate concentration was measured using Bio-Tek Synergy HT microplate reader at 450 nm and comparing to a standard curve.

Example 13: CELLTITER-GLO™ Luminescent ATP Quantification

PC3 or MSC cells were plated at a density of 10,000 cells per well in 96-well plates compatible with the luminometer used in 100 μL media. MITO-DCA (20 μM), TPP-DCA (60 μM), and Na-DCA (60 μM) were added to experimental wells, and incubated for 3 h at 37° C. in 5% $CO_2$ atmosphere.

Control wells containing medium without cells were prepared to obtain a value for background luminescence. Plates were then equilibrated at room temperature for ~30 min. A volume of CELLTITER-GLO™ reagent equal to the volume of cell culture medium present in each well was added, this mixtures were well mixed for 2 min using a shaker to induce cell lysis. The plates were allowed to incubate at room temperature for 10 min to stabilize luminescent signal. Luminescent was recorded using a plate reader. ATP quantification was carried out from a standard curve using ATP disodium salt hydrate.

Example 14: Generation of BMDCs

BMDCs were isolated from 6-8 weeks old C57BL/6 mice. After euthanization, bone marrows were isolated by flushing mouse femurs in RPMI. The harvested cells were centrifuged at 1250 rpm for 10 min and the pellet was resuspended in ice-cold 2 mL of buffer to lyse erythrocytes. The cells were counted, resuspended and transferred to petri dishes at the final concentration of $1.5 \times 10^6$ cells/mL. To this culture GM-CSF (20 ng/mL) was added to generate BMDCs. Media was changed on days 2 and 4. On day 6 cells were processed further to obtain pure DC population by subjecting cells to MACS bead purification using anti-CD11c antibody as per manufacturer's instructions. DC purity was tested by incubating BMDCs with LPS (100 ng/mL) and measured the surface expression of CD11c.

Example 15: Anti-Tumor Immunity Study by ELISA

PC3 cells were plated at the concentration of $0.5 \times 10^6$ cells/mL in six well plates and allowed to grow for 12 h. The cells were incubated with 150 µM Na-DCA, 150 µM TPP-DCA, and 50 µM MITO-DCA for 24 h at 37° C. PC3 supernatants were added to freshly prepared BMDCs ($0.5 \times 10^6$ cells/mL). BMDCs were incubated with the supernatants at 37° C. for 24 h. Additionally, LPS alone (100 ng/mL) was added to the DC cultures. The DCs were centrifuged at 1,800 RPM for 3 min and ELISA were performed on the supernatants against the cytokines IL-2, IL-4, IL-6, IL-10, IL-12, TNF-α, and IFN-γ according to manufacturer's protocol. Briefly, antibody coated plates were blocked with 10% FBS in PBS for 1 h at room temperature followed by washings. BMDC supernatants were incubated on the plates for 1 h at room temperature. This was immediately followed by washings and sequential incubations with the cytokine-biotin conjugate and streptavidin working solution. Finally, the substrate reagent containing 3,3',5,5' tetramethylbenzidine (100 µL) was added to each well, incubated for 30 min, the reaction was stopped by adding 50 µL stop solution containing 0.1 M $H_2SO_4$. The absorbance was recorded at 450 nm using a BioTek Synergy HT well plate reader.

Example 16: Synthesis of PLGA-Tris-DCA

Dichloroacetic acid (DCA) was covalently attached to the hydrophobic PLGA polymer through ester linkage. In order to achieve high reproducibility and better loading efficiencies of the drugs to the polymeric platform, PLGA was functionalized with Tris molecule bearing three sites to attach drugs covalently. Individual drugs were attached to using simple eater linkage to the PLGA-Tris platform. As an example synthesis of PLGA-Tris-DCA has been illustrated below.

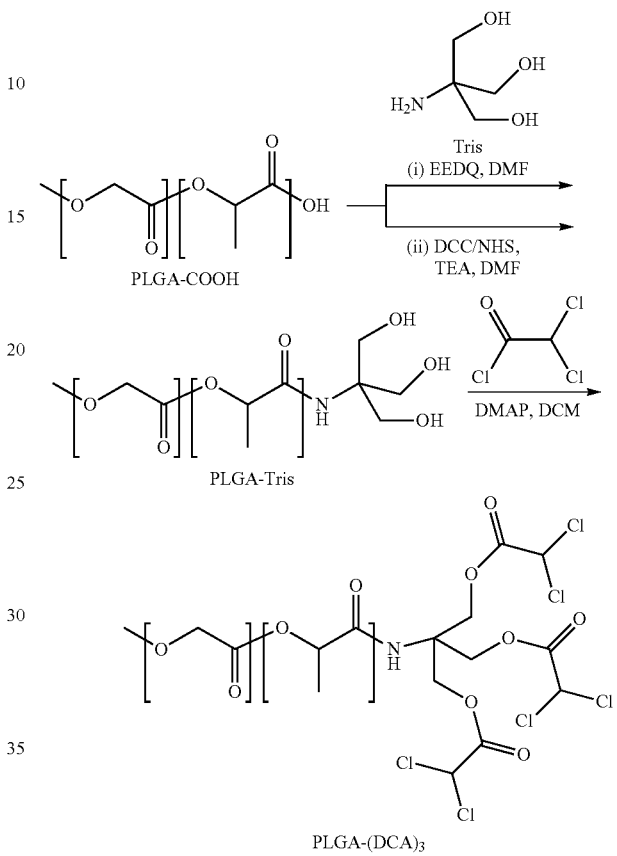

Example 17: Synthesis of PLGA-Tris

A mixture of PLGA-COOH (inherent viscosity d/L 0.15-0.25) (500 mg, 0.090 mmol) and NHS (12.37 mg, 0.107 mmol) in dry $CH_2Cl_2$ was stirred for 30 min at 0° C. A solution of DCC (20.34 mg, 0.098 mmol) in $CH_2Cl_2$ was added drop wise to the reaction mixture. The reaction was stirred from 0° C. to room temperature for 12 h. The precipitated N,N'-dicyclohexylurea (DCU) by-product was filtered off and the solution was evaporated using rotavap. This residue was dissolved in dry $CH_2Cl_2$. A solution of triethylamine (18.13 mg, 0.18 mmol) and Tris (22.0 mg, 0.18 mmol) in 10 mL DMF was added slowly to the above reaction mixture. This reaction mixture was kept at room temperature for 24 h with vigorous stirring. The solvent was evaporated to dryness. The residue was dissolved in CH2Cl2, filtered and precipitated with diethyl ether and methanol ($CH_2Cl_2$:MeOH:diethyl ether: 1:5:4). This process was repeated 5 times. Yield, 190 mg, 37%. 1H NMR (CDCl3, 400 MHz): δ ppm 5.20 (m), 4.81 (m), 4.28 (br), 3.66 (s), 1.56 (d).

Example 18: Synthesis of PLGA-Tris-(DCA)3

A mixture of PLGA-Tris (100 mg, 0.016 mmol) and DMAP (10.14 mg, 0.083 mmol) in dry $CH_2Cl_2$ was stirred for 30 min at room temperature. A solution of dichloroacetyl chloride (49.13 mg, 0.33 mmol) in CH$_2$Cl$_2$ was added drop wise to the reaction mixture. The reaction was stirred at room temperature for 24 h. The solvent was evaporated to dryness. The residue was dissolved in CH$_2$Cl$_2$, precipitated with diethyl ether and methanol (CH$_2$Cl$_2$:MeOH:diethyl ether: 1:5:4). This process was repeated 5 times. Yield, 40 mg, 38%. $^1$H NMR (CDCl$_3$, 400 MHz): δ ppm 6.07 (s), 6.03 (s), 5.22 (m), 4.82 (m), 1.59 (m).

Example 19: Synthesis of PSMA Targeting Polymer

Figure 9:
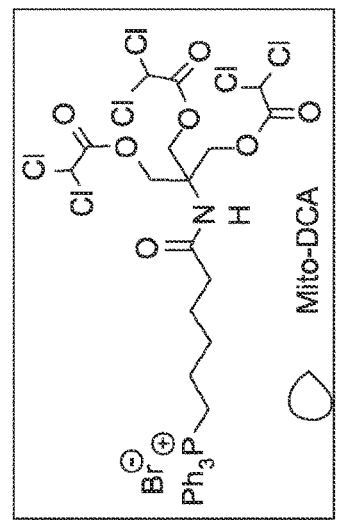
FIG. 9 is a cartoon showing PSMA targeting polymer forming a nanoparticle encapsulating MITO-DCA.
Figure 9:
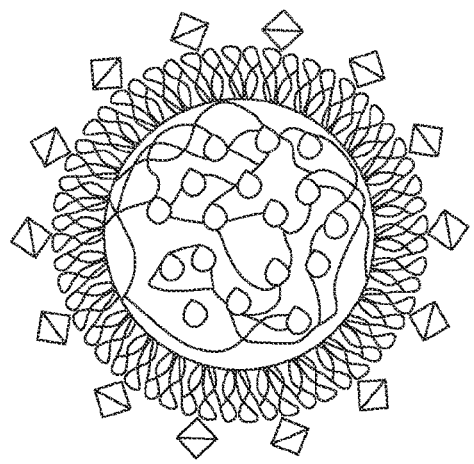
Figure 9:
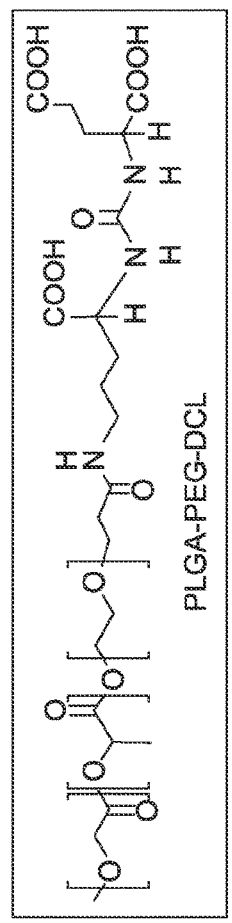
Figure 9:
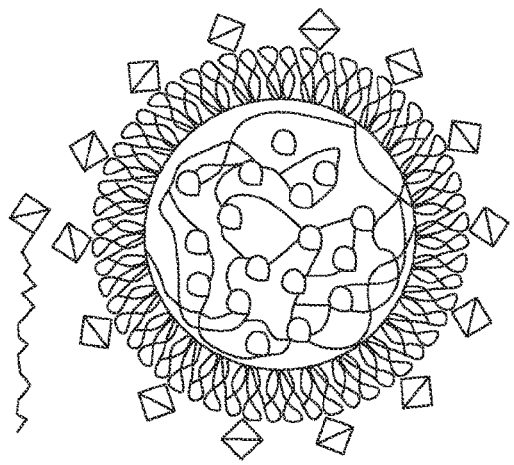

The synthesis of PSMA targeting polymer is shown below. PSMA is a targeting moiety (TC). The compounds disclosed herein can be encapsulated in nanoparticles of the resulting PLGA-PEG-DCL as shown in FIG. 9.

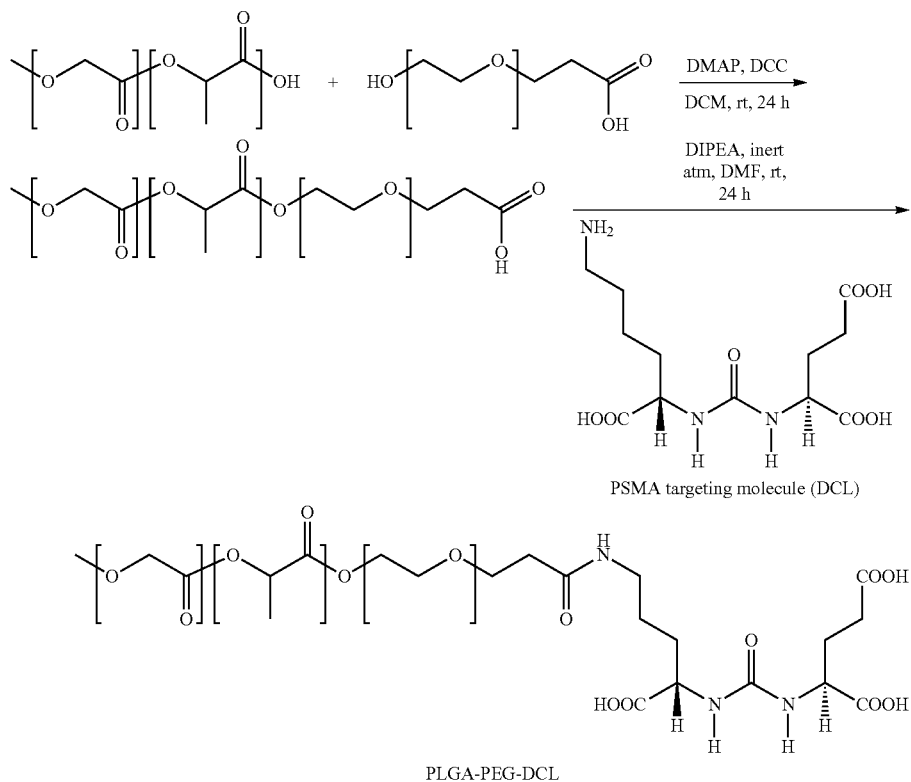

PLGA-PEG-DCL

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

What is claimed is:

1. A compound having Formula I the following formula:

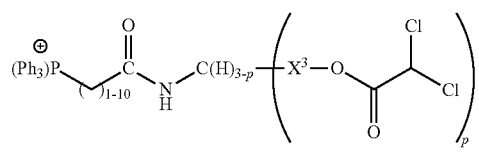

where p is from 1 to 3; and

X$^3$ is a linker or a pharmaceutically acceptable salt thereof.

2. The compound of claim 1, wherein the compound is:

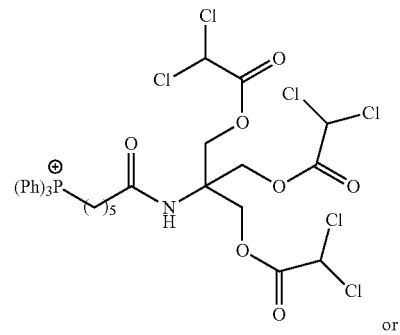

or

-continued

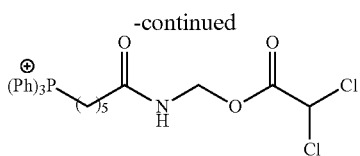

or a pharmaceutically acceptable salt thereof.

3. A composition, comprising a compound of claim 1 and a pharmaceutically acceptable carrier.

4. A nanoparticle comprising a hydrophobic core, a hydrophilic outer layer surrounding the core, and a compound of claim 1.

5. The nanoparticle of claim 4, wherein the core comprises poly(lactic-co-glycolic) acid.

6. The nanoparticle of claim 4, wherein the hydrophilic outer layer comprises polyethylene glycol and is attached to the core.

7. The compound of claim 1, wherein $X^3$ is $CH_2$.

8. The compound of claim 1, wherein the compound has Formula III

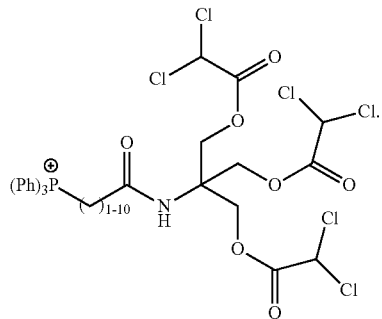

* * * * *